(12) United States Patent
Fukuma et al.

(10) Patent No.: US 9,789,312 B2
(45) Date of Patent: Oct. 17, 2017

(54) RETINAL PROSTHESIS SYSTEM

(71) Applicant: KABUSHIKI KAISHA TOPCON, Tokyo (JP)

(72) Inventors: Yasufumi Fukuma, Wako (JP); Hisashi Tsukada, Hachioji (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 14/914,440

(22) PCT Filed: Jul. 29, 2014

(86) PCT No.: PCT/JP2014/069932
§ 371 (c)(1),
(2) Date: Feb. 25, 2016

(87) PCT Pub. No.: WO2015/040958
PCT Pub. Date: Mar. 26, 2015

(65) Prior Publication Data
US 2016/0213926 A1    Jul. 28, 2016

(30) Foreign Application Priority Data

Sep. 18, 2013  (JP) .................................. 2013-193467

(51) Int. Cl.
A61N 1/36    (2006.01)
A61N 1/05    (2006.01)
A61N 1/378   (2006.01)

(52) U.S. Cl.
CPC ....... *A61N 1/36046* (2013.01); *A61N 1/0543* (2013.01); *A61N 1/378* (2013.01); *A61F 2250/0001* (2013.01)

(58) Field of Classification Search
CPC ... A61N 1/0543; A61N 1/36046; G02B 1/043
See application file for complete search history.

(56) References Cited

U.S. PATENT DOCUMENTS

| 6,427,087 B1 | 7/2002 | Chow et al. |
| 2004/0102843 A1* | 5/2004 | Yagi .......................... A61F 2/14 623/4.1 |

(Continued)

FOREIGN PATENT DOCUMENTS

| JP | 2003-531697 | 10/2003 |
| JP | 2006-517828 | 8/2006 |

(Continued)

OTHER PUBLICATIONS

International Search Report for PCT/JP2014/069932 date Sep. 2, 2014, 4 pgs.

(Continued)

*Primary Examiner* — Michael Carey
*Assistant Examiner* — Natasha Patel
(74) *Attorney, Agent, or Firm* — Procopio, Cory, Hargreaves & Savitch LLP

(57) ABSTRACT

A retinal prosthesis system according to an embodiment includes a converter, a retinal prosthesis, and a transmitter. The converter is placed in an eye, and transmits part of light incident on the eye therethrough while converting the energy of the other part of the light into electrical energy. The retinal prosthesis is placed in the eye and includes a photoelectric conversion element array configured to operate with the electrical energy received from the converter to detect the light having transmitted through the converter to generate an electrical signal. The transmitter is used to send the electrical signal generated by the retinal prosthesis to the visual cortex of the brain.

6 Claims, 10 Drawing Sheets

(56) References Cited

U.S. PATENT DOCUMENTS

| | | | |
|---|---|---|---|
| 2004/0181265 A1 | 9/2004 | Palanker et al. | |
| 2005/0134796 A1* | 6/2005 | Zelvin | A61B 3/12 351/206 |
| 2008/0208335 A1 | 8/2008 | Blum et al. | |
| 2009/0033863 A1* | 2/2009 | Blum | A61F 2/14 351/159.34 |
| 2013/0218271 A1* | 8/2013 | Wu | A61N 1/36046 623/6.63 |
| 2013/0282119 A1 | 10/2013 | Pagani | |
| 2015/0301338 A1* | 10/2015 | Van Heugten | G02C 7/04 345/8 |

FOREIGN PATENT DOCUMENTS

| | | |
|---|---|---|
| JP | 2008-079799 | 4/2008 |
| JP | 2010-517081 | 5/2010 |
| WO | 2012090188 A1 | 7/2012 |

OTHER PUBLICATIONS

Mitsunaga, S., et al., Organic Thin-Film Solar Cell Technologies for Realization of Low-Cost and High-Performance Solar Cells, Toshiba Review, 67(1), 2012, 4 pgs.

Mitsunaga, S., et al., Organic Thin-Film Solar Cell Technologies for Realization of Low-Cost and High-Performance Solar Cells, Toshiba Review, 67(1), 2012, English translation, 6 pgs.

Office Action for Japan Patent Application No. JP 2013-193467 dated Jul. 18, 2017. 6 pages. Japan Patent Office.

* cited by examiner

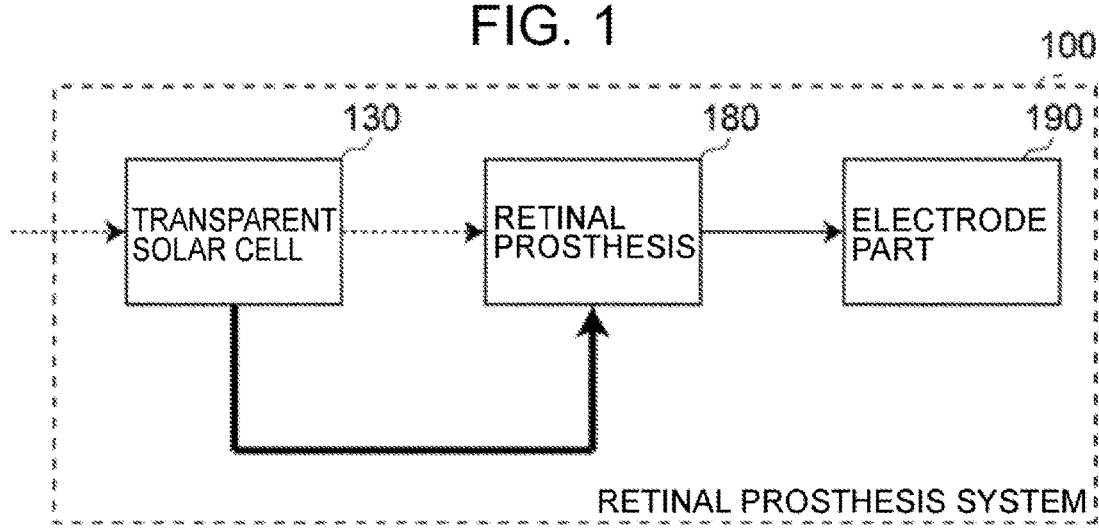
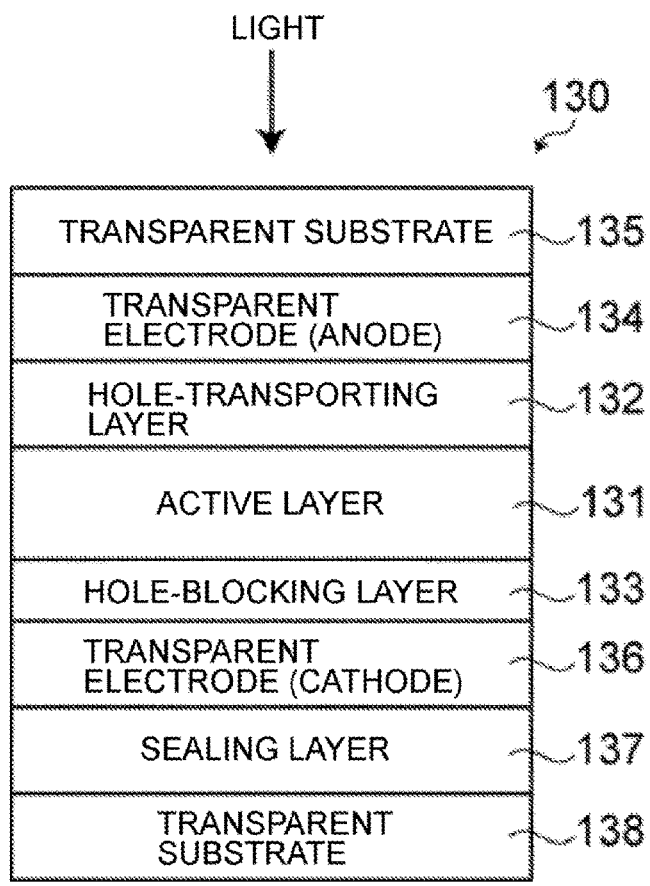

RETINAL PROSTHESIS SYSTEM

CROSS-REFERENCE TO RELATED APPLICATIONS

This application is a U.S. National Stage Application of International Application Ser. No. PCT/JP2014/069932, filed Jul. 29, 2014, which claims benefit of priority from Japanese application Ser. No. JP2013-193467, filed Sep. 18, 2013, the contents of which are incorporated by reference.

TECHNICAL FIELD

Embodiments described herein relate generally to a retinal prosthesis system including retinal prosthesis to be implanted in the eye.

BACKGROUND ART

Vision is one of the human senses which has a substantial impact on the quality of life (QOL), and disorders thereof significantly impair the QOL. Therefore, for those having vision disorders, there is a need for the establishment of a technology to complement the lost function. Retinal prosthesis is known as such a technology.

Patent Document 1 discloses a retinal prosthesis including a photodiode for generating an electrical signal from incident light, and a thin film transistor for transmitting the electrical signal generated by the photodiode to the optic nerve. In the retinal prosthesis, a three-dimensional structure is obtained by stacking semiconductor layers, in which various elements are formed, to allow the photodiode to have a larger size.

Patent Document 2 discloses a retinal prosthesis which is implanted inside the eye having a retina. The retinal prosthesis includes a stimulus array arranged in the central region of the retina, and a photovoltaic cell located in the outside of the macular area of the retina or the like. The photovoltaic cell generates power in response to ambient light. The stimulus array utilizes the power generated by the photovoltaic cell.

[Patent Document 1] Japanese Unexamined Patent Application Publication No. 2008-79799

[Patent Document 2] Japanese Unexamined Patent Application Publication (Translation of PCT Application) No. 2006-517828

SUMMARY OF THE INVENTION

Problems to be Solved by the Invention

In the eye, for converting the energy of incident light into electrical energy so that a retinal prosthesis can operate by receiving the electrical energy, it is desirable to ensure as wide space as possible to perform the conversion while the size of the retinal prosthesis is increased to a certain extent. However, in the technologies disclosed in Patent Documents 1 and 2, it is difficult to secure both of a space for the placement of the retinal prosthesis in a desired size and a space for the conversion of the energy of light into electrical energy in the eye.

The present invention has been made to solve the above problem, and one object thereof is to provide a technology capable of securing a space for the placement of a retinal prosthesis in a desired size as well as a space for converting the energy of light into electrical energy in the eye.

Means of Solving the Problems

A retinal prosthesis system of an embodiment includes: a converter configured to be placed in an eye, and allow part of light incident on the eye to pass therethrough while converting the energy of the other part of the light into electrical energy; a retinal prosthesis configured to be placed in the eye, including a photoelectric conversion element array configured to operate with the electrical energy received from the converter to detect the light having passed through the converter to generate an electrical signal; and a transmitter configured to send the electrical signal generated by the retinal prosthesis to the visual cortex of the brain.

BRIEF DESCRIPTION OF THE DRAWINGS

FIG. 1 is a schematic diagram illustrating an example of the configuration of a retinal prosthesis system according to an embodiment.

FIG. 2 is a schematic diagram illustrating an example of the configuration of a retinal prosthesis system according to an embodiment.

MODES FOR CARRYING OUT THE INVENTION

Figure 3:
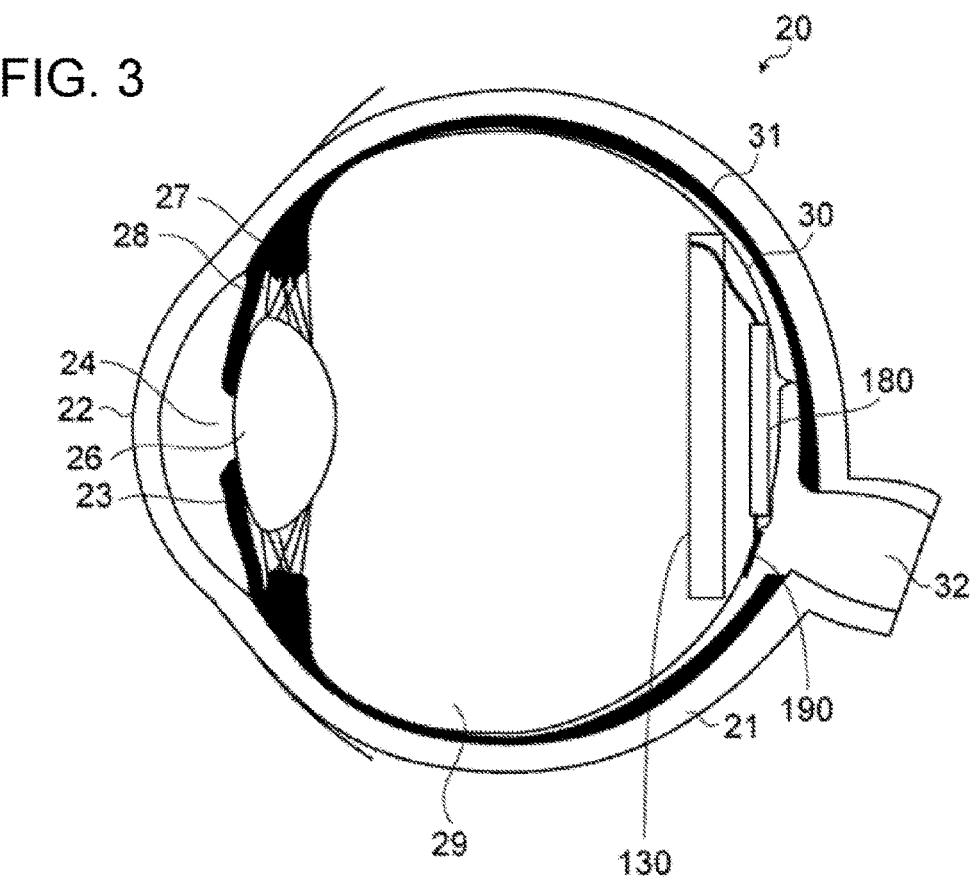
FIG. 3 is a schematic diagram illustrating an example of the configuration of a retinal prosthesis system according to an embodiment.

A description is given in detail of a retinal prosthesis system according to exemplary embodiments with reference to the accompanying drawings. The retinal prosthesis system of an embodiment includes a retinal prosthesis, which is configured to be placed within the eye and operate with electrical energy converted from the energy of light incident on the eye. The disclosure of the references cited in this specification may be incorporated herein by reference.

<First Embodiment>
[Configuration]

FIG. 1 is a functional block diagram illustrating an example of the configuration of a retinal prosthesis system according to a first embodiment. In FIG. 1, the path of light is indicated by a broken arrow in distinction from the paths of others (e.g., electrical signal, etc.) each indicated by a solid line. A retinal prosthesis system 100 includes a transparent solar cell 130, a retinal prosthesis 180, and an electrode part 190. The retinal prosthesis system 100 is placed inside the eye.

The transparent solar cell 130 lets part of light incident on the eye transmit therethrough, and converts the energy of other part of the light into electrical energy. The retinal prosthesis 180 includes a photoelectric conversion element array configured to operate with the electrical energy obtained by the transparent solar cell 130 to detect the light having transmitted through the transparent solar cell 130 to generate an electrical signal. The electrode part 190 is used to send the electrical signal generated by the retinal prosthesis 180 to the visual cortex of the brain. A power supply line is provided between the transparent solar cell 130 and the retinal prosthesis 180 to supply the electric power (electrical energy) generated by the transparent solar cell 130. Besides, a signal line is provided between the retinal prosthesis 180 and the electrode part 190 to transmit the electrical signal to be sent to the visual cortex of the brain. The term "pass" as used herein includes the meaning of "transmit", and "pass" and "transmit" may be used as the same meaning. Further, the terms "electrical energy" and "(electrical) power" as used herein may be deemed to be the same.

(Transparent Solar Cell)

The transparent solar cell 130 is formed using, for example, the organic thin-film technology.

FIG. 2 schematically illustrates an example of the sectional structure of the transparent solar cell 130 of the first embodiment. The transparent solar cell 130 has a structure in which an active layer 131 for generating electric power by receiving light is sandwiched between a hole-transporting layer 132 and a hole-blocking layer 133. The hole-transporting layer 132 is formed on the light-receiving surface side with respect to the active layer 131. The hole-blocking layer 133 is formed on the side opposite to the hole-transporting layer 132 with respect to the active layer 131. A transparent electrode 134 serving as an anode is formed on the light-receiving surface side of the hole-transporting layer 132. A transparent substrate 135 is arranged on the light-receiving surface side of the transparent electrode 134. Meanwhile, a transparent electrode 136 as a cathode is formed on the side opposite to the light receiving surface of the hole-blocking layer 133. The element including the transparent substrate 135, the transparent electrode 134, the hole-transporting layer 132, the active layer 131, the hole-blocking layer 133, and the transparent electrode 136 is sealed by a sealing layer 137 made of a transparent epoxy resin and a transparent substrate 138.

The active layer 131 can be formed by dissolving a p-type organic semiconductor and an n-type organic semiconductor in an organic solvent, and applying it by spin coating. The active layer 131 thus formed has a bulk heterojunction structure. The light incident on the transparent solar cell 130 is absorbed in the active layer 131. In the active layer 131, excitons are generated by photoexcitation in, for example, the n-type organic semiconductor. The excitons are diffused in the n-type organic semiconductor. The excitons diffused to the pn junction interface are dissociated into holes and electrons. The holes are dispersed in the p-type organic semiconductor, and are transported in the hole-transporting layer 132 to the transparent electrode 134. Meanwhile, the electrons are dispersed in the n-type organic semiconductor, and are transported in the hole-blocking layer 133 to the transparent electrode 136. As a result, a potential difference is generated between the transparent electrode 134 and the transparent electrode 136.

The hole-transporting layer 132 suppresses the deactivation caused by the recombination of holes and electrons resulted from the movement of the holes and the electrons to the anode side. The hole-blocking layer 133 suppresses the deactivation caused by the recombination of holes and electrons resulted from the movement of the holes and the electrons to the cathode side.

For more information about a technology related to a cell such as the transparent solar cell 130, reference may be had to, for example, "Organic thin-film solar cell technologies for realization of low-cost and high-performance solar cells" (Saito Mitsunaga et al., Toshiba Review, Vol. 67 No. 1 (2012), p. 30-33).

With the configuration described above, the transparent solar cell 130 can transmit part of the light incident on the eye therethrough, and convert the energy of other part into electrical energy. As described below, by forming an opening, the transparent solar cell 130 can transmit part of the light incident on the eye therethrough, and convert the energy of other part of the light into electrical energy. The transparent solar cell 130 is an example of the "converter".

(Retinal Prosthesis)

The retinal prosthesis 180 is provided with a photoelectric conversion element array, and outputs an electrical signal generated by a photoelectric conversion element that has received the light having transmitted through the transparent solar cell 130. The photoelectric conversion element array includes, for example, a matrix of a plurality of photoelectric conversion elements. A retinal prosthesis having a known structure can be used as the retinal prosthesis 180. The retinal prosthesis 180 is an example of the "retinal prosthesis".

(Electrode Part)

The electrode part 190 includes, for example, a matrix of a plurality of stimulating electrodes. Each of the stimulation electrodes corresponds to one of the photoelectric conversion elements of the retinal prosthesis 180. Each of the stimulation electrodes is electrically connected to corresponding one of the photoelectric conversion elements. The stimulation electrodes are implanted to stimulate the retina and the optic nerve in the eye with the electrical signal generated by the retinal prosthesis 180. For example, the stimulation electrodes are implanted such that the electrical signal is transmitted to the photoreceptor cells, the retinal ganglion cells, or the bipolar cells. The electrode part 190 is an example of the "transmitter".

[Arrangement Example]

FIG. 3 is a schematic cross-sectional view of an eye in which the retinal prosthesis system 100 of the first embodiment is placed. Specifically, FIG. 3 is a cross sectional view of the right eye as viewed from the above. Like reference numerals designate like parts as in FIG. 1, and the same description may not be repeated. For convenience of explanation, FIG. 3 may not illustrate power lines and signal lines provided between parts of the retinal prosthesis system 100.

An eye 20 has a substantially spherical shape and the outer is covered by a sclera 21. The light incident from the front of the eye 20 is refracted by a cornea 22, and passes through a pupil 24, whose size has been adjusted by an iris 23. As the light is passing through the pupil 24, the amount of light projected on a retina 30 is adjusted. The light having passed through the pupil 24 is incident on a (crystalline) lens 26. The thickness of the lens 26 varies through a through a ciliary zonule 28 according to the movement (tensed or relaxed state, etc.) of a ciliary body 27. The light having passed through the pupil 24 is refracted again by the lens 26, the refractive power of which varies depending on the thickness.

After having been refracted by the lens 26, the light passes through a vitreous body 29 and reaches the transparent solar cell 130. The transparent solar cell 130 transmits part of the incident light therethrough, and converts the energy of other part into electrical energy. The electrical energy obtained by the transparent solar cell 130 is supplied to the retinal prosthesis 180 that implements the function of the retina 30, which is supplied with oxygen, nutrition, and the like by a choroid 31. The light having transmitted through the transparent solar cell 130 reaches the retinal prosthesis 180. The light having reached the retinal prosthesis 180 is converted into an electrical signal. The electrical signal generated by the retinal prosthesis 180 is sent via the electrode part 190 to the photoreceptor cells, the retinal ganglion cells, or the bipolar cells, or is sent to the brain via an optic nerve 32.

As described above, in this embodiment, the transparent solar cell 130 is located between the lens 26 and the retinal prosthesis 180. The retinal prosthesis 180 generates an electrical signal corresponding to the light having passed through the transparent solar cell 130. With this, the transparent solar cell 130 and the retinal prosthesis 180 do not limit their sizes each other, and thus both the sizes can be sufficiently secured. Besides, a structure can be employed in which the retinal prosthesis 180 is located in the vicinity of the fundus, and the transparent solar cell 130 is located in front thereof (on the cornea side). This allows an increase in the size of the transparent solar cell 130. Further, by ensuring the size of the retinal prosthesis 180, more information can be transmitted through the optic nerve.

Although this embodiment describes an example in which the transparent solar cell 130 transmits light incident on the eye therethrough, and the retinal prosthesis 180 receives the light having transmitted through the transparent solar cell 130 directly to perform photoelectric conversion, this is not a limitation. For example, a configuration may be employed in which the transparent solar cell 130 transmits light incident on the eye therethrough and the retinal prosthesis 180 receives the light having transmitted through the transparent solar cell 130 indirectly to perform photoelectric conversion. As an example of the case where the retinal prosthesis 180 indirectly receives the light having transmitted through the transparent solar cell 130, the light incident on the eye is reflected by a reflector (optical element), such as a reflective mirror, one or several times to be received by the retinal prosthesis 180. The reflector may be located on the cornea side with respect to the transparent solar cell 130. If a reflector is provided in the eye, each of the transparent solar cell 130 and the retinal prosthesis 180 may be efficiently arranged in the eye.

[Effects]

The retinal prosthesis system 100 is an example of the retinal prosthesis system of this embodiment. Described below are the effects of the retinal prosthesis system of this embodiment.

The retinal prosthesis system (e.g., the retinal prosthesis system 100) includes a converter (e.g., the transparent solar cell 130), a retinal prosthesis (e.g., the retinal prosthesis 180), and a transmitter (e.g., the electrode part 190). The converter is placed in the eye, and configured to transmit part of light incident on the eye therethrough and convert the energy of other part of the light into electrical energy. Here, "other part of the light" may include the entire part of the light incident on the eye excluding the part of the light that transmits through the converter. The retinal prosthesis is placed in the eye, and includes a photoelectric conversion element array configured to operate with the electrical energy received from the converter to detect the light having transmitted through the converter to generate an electrical signal. The transmitter is used to send the electrical signal generated by the retinal prosthesis to the visual cortex of the brain.

In the retinal prosthesis system, the converter placed in the eye passes (transmits) part of light incident on the eye therethrough and converts the energy of other part of the light into electrical energy. The retinal prosthesis can operate with the electrical energy received from the converter. At this time, the retinal prosthesis can directly or indirectly receive the light having passed through the converter. As an example of the case where the retinal prosthesis directly receives the light having transmitted through the converter, in the configuration in which the retinal prosthesis is located in the vicinity of the fundus and the converter is located on the cornea side, the light incident on the eye may pass through the converter, and the light having passed through the converter may be incident on the retinal prosthesis. Meanwhile, as an example of the case where the retinal prosthesis indirectly receives the light having transmitted through the converter, in the configuration in which the retinal prosthesis is located in the vicinity of the fundus and the converter is located on the cornea side, the light incident on the eye may pass through the converter, and the light having passed through the converter may be reflected by a reflector (an optical element such as the surface of the cornea and a reflective mirror) to be incident on the retinal prosthesis. With this, differently from the technology disclosed in Patent Document 2, in which the retinal prosthesis and the photovoltaic cell are located in the fundus, the converter can be located on the cornea side in the eye with respect to the retinal prosthesis located in the vicinity of the fundus. Thereby, the converter and the retinal prosthesis can be arranged on the axis of the light incident on the eye. Accordingly, the converter and the retinal prosthesis do not limit their sizes each other, and thus both a space for the placement of the retinal prosthesis in a desired size and a space for converting the energy of light into electrical energy can be ensured in the eye.

In the retinal prosthesis system, the converter may include a transparent solar cell (e.g., the transparent solar cell 130). The transparent solar cell is configured to transmit part of light incident on the eye and convert the energy of other part into electrical energy. The photoelectric conversion element array is configured to receive the light having transmitted through the transparent solar cell and generate an electrical signal.

In the retinal prosthesis system, the converter transmits part of light incident on the eye therethrough. The photoelectric conversion element array included in the retinal prosthesis receives the light having transmitted through the converter and generates an electrical signal. This makes it possible to secure a space for the placement of the retinal prosthesis in a size to ensure required light as well as a space for the placement of the converter in which as wide a light receiving surface as possible is ensured.

<Second Embodiment>

In the first embodiment, the converter for converting light energy into electrical energy is described as being transmissive by way of example. However, the converter may be non-transmissive. In the following, a retinal prosthesis system according to a second embodiment is described focusing on differences from the first embodiment.

[Configuration]

Figure 4:
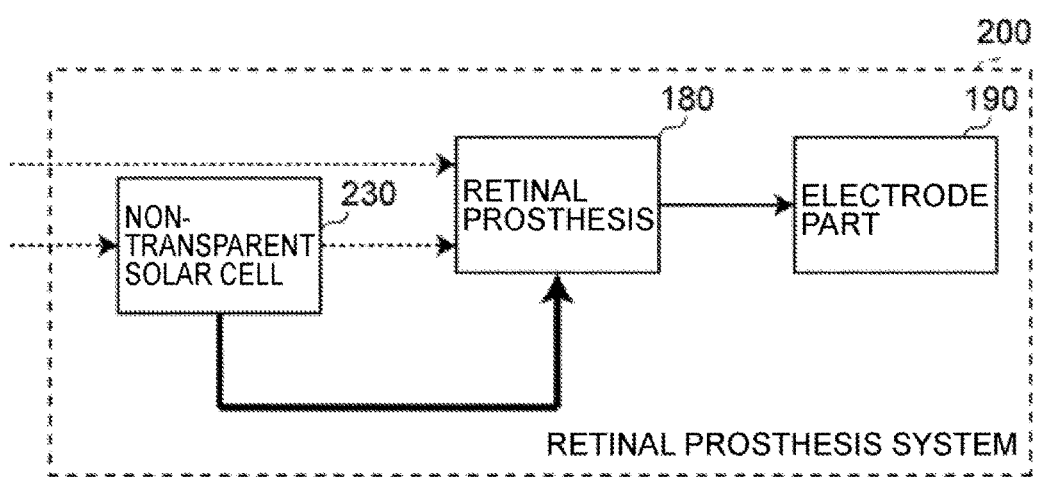
FIG. 4 is a schematic diagram illustrating an example of the configuration of a retinal prosthesis system according to an embodiment.

FIG. 4 is a functional block diagram illustrating an example of the configuration of a retinal prosthesis system according to the second embodiment. In FIG. 4, like reference numerals designate like parts as in FIG. 1, and the same description may not be repeated. In FIG. 4, the path of light is indicated by a broken arrow in distinction from the paths of others (e.g., electrical signal, etc.) each indicated by a solid line.

A retinal prosthesis system 200 includes a non-transparent solar cell 230, the retinal prosthesis 180, and the electrode part 190. As with the retinal prosthesis system 100, the retinal prosthesis system 200 is placed in the eye. The retinal prosthesis system 200 is different from the retinal prosthesis system 100 in being provided with the non-transparent solar cell 230 in place of the transparent solar cell 130. For example, the non-transparent solar cell 230 may have a different size or shape from that of the transparent solar cell 130 to allow part of light incident on the eye to pass therethrough. For example, if the non-transparent solar cell 230 is smaller, light incident on the eye can pass through it. For another example, if the non-transparent solar cell 230 has an opening or a cutout as described below, light incident on the eye can pass through it. Besides, the non-transparent solar cell 230 may be arranged to avoid crossing over the path of light projected on the fundus center or the macula.

A power supply line is provided between the non-transparent solar cell 230 and the retinal prosthesis 180 to supply electric power generated by the non-transparent solar cell 230. In addition, a signal line is provided between the retinal prosthesis 180 and the electrode part 190 to transmit the electrical signal to be sent to the visual cortex of the brain.

In this embodiment, one or more openings are formed in the non-transparent solar cell 230.

Figure 5:
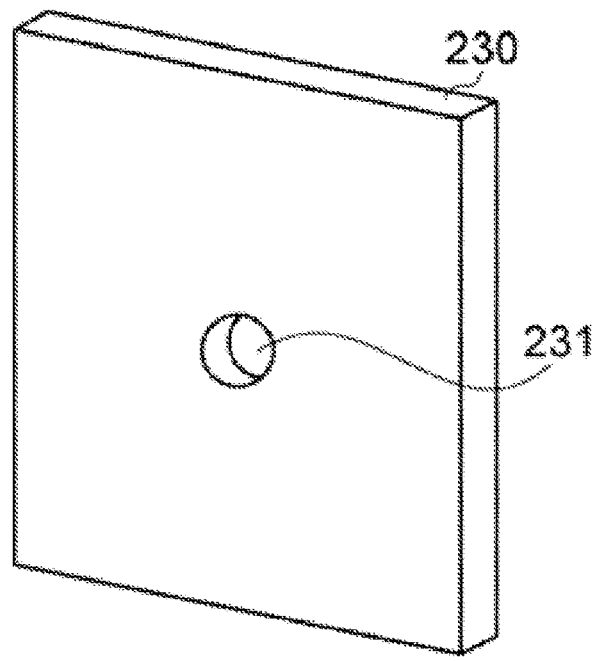
FIG. 5 is a schematic diagram illustrating an example of the configuration of a retinal prosthesis system according to an embodiment.
Figure 6:
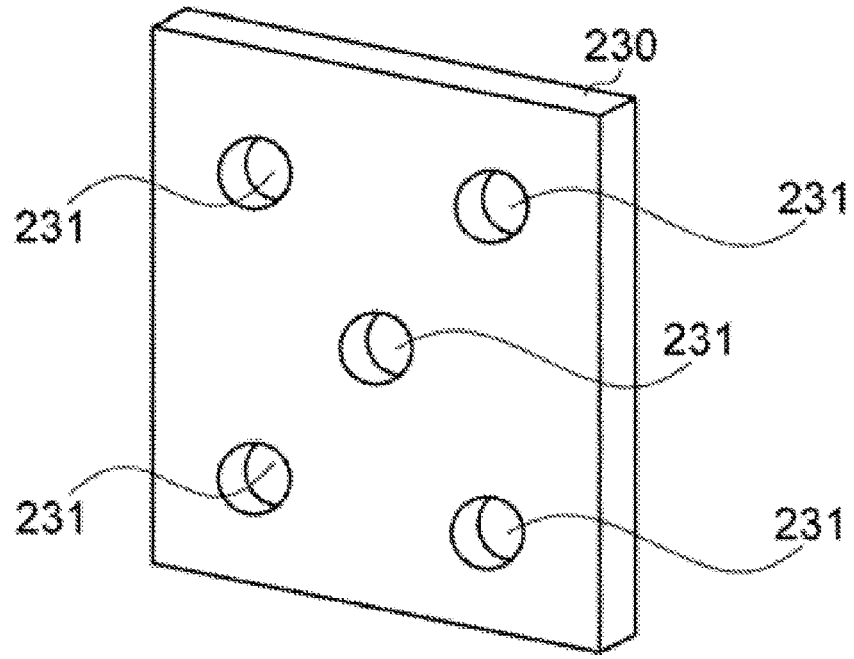
FIG. 6 is a schematic diagram illustrating an example of the configuration of a retinal prosthesis system according to an embodiment.

FIGS. 5 and 6 illustrate an example of the structure of the non-transparent solar cell 230 of the second embodiment. FIGS. 5 and 6 schematically illustrate the non-transparent solar cell 230 that is placed perpendicular to the predetermined axis O of the retinal prosthesis system 200. As illustrated in FIG. 5, the non-transparent solar cell 230 is provided with an opening 231 that is formed in a position where light along the predetermined axis O of the retinal prosthesis system 200 and light around it pass through. Besides, as illustrated in FIG. 6, a plurality of openings 231 may be formed in the non-transparent solar cell 230.

As illustrated in FIG. 5 or 6, the light incident on the eye passes through the opening(s) 231 formed in the non-transparent solar cell 230, and reaches the vitreous body 29.

The non-transparent solar cell 230 includes an active layer, a hole-transporting layer, and a hole-blocking layer similar to those of the transparent solar cell 130, which are sealed by a non-transparent electrode, a substrate, a sealing layer, and the like. The non-transparent solar cell 230 is an example of the "converter".

In this embodiment, the non-transparent solar cell 230 may be provided with the opening(s) 231 formed in a position opposite to the macula in the retinal prosthesis 180 such that the light having passed through the opening(s) 231 can reach the macula where photoreceptor cells are present at high density. This enables to ensure the amount of light that reaches the macula.

In this embodiment, although the non-transparent solar cell 230 is described as being provided with an opening(s), the non-transparent solar cell 230 may be provided with a cutout. Further, in this embodiment, while the non-transparent solar cell 230 is described as being provided with one or more openings, the transparent solar cell 130 of the first embodiment may be provided with one or more openings or cutouts.

[Effects]

The retinal prosthesis system 200 is an example of the retinal prosthesis system of this embodiment. Described below are the effects of the retinal prosthesis system of this embodiment.

In the retinal prosthesis system (e.g., the retinal prosthesis system 200), the converter may include a non-transparent solar cell (e.g., the non-transparent solar cell 230). The converter is configured to allow part of light incident on the eye to pass therethrough and convert the energy of other part of the light into electrical energy. Here, "other part of the light" may include the entire part of the light incident on the eye excluding the part of the light that transmits through the converter. The photoelectric conversion element array included in the retinal prosthesis receives the light having passed through the converter (the non-transparent solar cell) and generates an electrical signal.

In the retinal prosthesis system, the light incident on the eye reaches the retinal prosthesis after having passed through the converter. Thereby, the converter and the retinal prosthesis can be arranged on the axis of the light incident on the eye. Accordingly, the converter and the retinal prosthesis do not limit their sizes each other, and thus both a space for the placement of the retinal prosthesis in a desired size and a space for converting the energy of light into electrical energy can be ensured in the eye. Further, since the retinal prosthesis is located in the vicinity of the fundus, and the converter is located in front thereof (on the cornea side), the light receiving surface of the converter can be increased in size as needed. Further, by ensuring the size of the retinal prosthesis, more information can be transmitted through the optic nerve.

In the retinal prosthesis system, the converter may be provided with an opening (e.g., the opening 231).

In the retinal prosthesis system, while the size of the converter is increased without limiting the size of the retinal prosthesis, both a space for the placement of the retinal prosthesis in a desired size and a space for converting the energy of light into electrical energy can be ensured.

In the retinal prosthesis system, the opening may be formed in a position opposite to the macula in the retinal prosthesis.

With the retinal prosthesis system, it is possible to ensure the amount of light that reaches the macula without limiting the sizes of both the converter and the retinal prosthesis.

In the retinal prosthesis system, the converter may include a transparent solar cell (e.g., the transparent solar cell 130). The converter (the transparent solar cell) is configured to transmit part of light incident on the eye therethrough and convert the energy of other part of the light into electrical energy. The photoelectric conversion element array included in the retinal prosthesis receives the light having transmitted through the converter and generates an electrical signal.

In the configuration in which the converter includes a transparent solar cell, the converter may be provided with an opening (e.g., the opening 231) to allow part of light incident on the eye to pass therethrough. The opening may be formed in a position opposite to the macula in the retinal prosthesis.

<Third Embodiment>

In the above embodiments, an example is described in which the retinal prosthesis 180 operate with the electrical energy generated by the transparent solar cell 130 or the like. The retinal prosthesis system may further include a lens that is driven to operate with the electrical energy generated by the transparent solar cell 130 or the like. In a third embodiment, light is refracted by the lens provided in place of the crystalline lens 26 to be incident on the transparent solar cell 130 or the non-transparent solar cell 230. In the following, a retinal prosthesis system according to the third embodiment is described focusing on differences from the first embodiment.

[Configuration]

Figure 7:
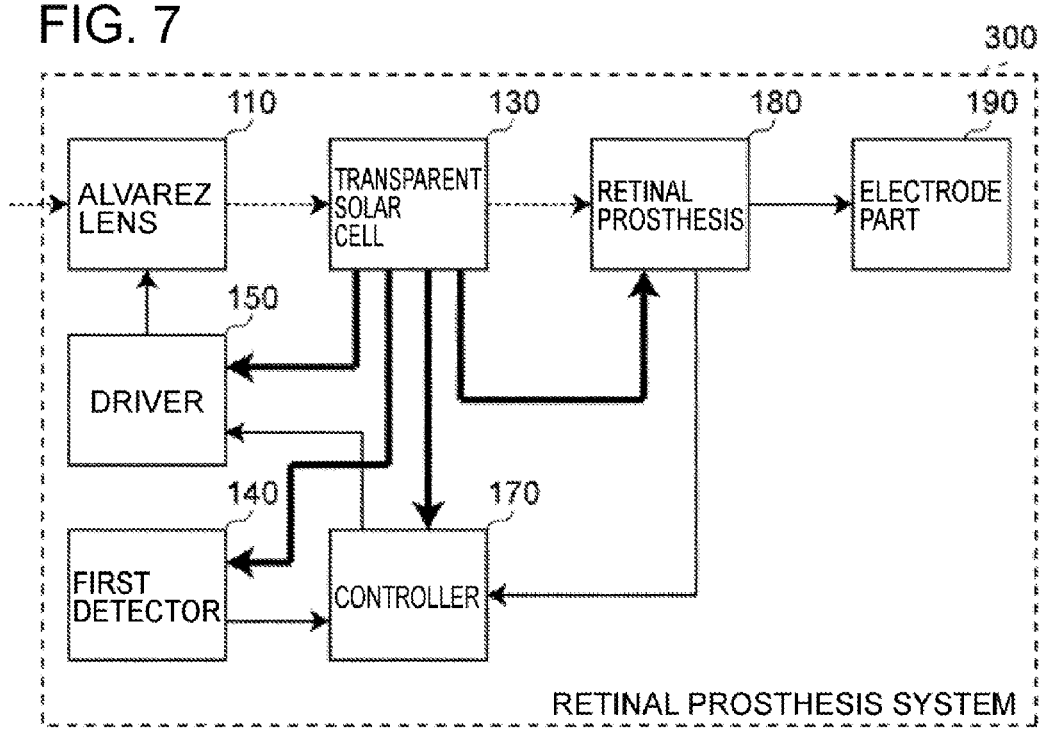
FIG. 7 is a schematic diagram illustrating an example of the configuration of a retinal prosthesis system according to an embodiment.

FIG. 7 is a functional block diagram illustrating an example of the configuration of a retinal prosthesis system according to the third embodiment. In FIG. 7, like reference numerals designate like parts as in FIG. 1, and the same description may not be repeated. In FIG. 7, the path of light is indicated by a broken arrow in distinction from the paths of others (e.g., electrical signal, etc.) each indicated by a solid line. A retinal prosthesis system 300 includes an Alvarez lens 110, the transparent solar cell 130, a first detector 140, a driver 150, a controller 170, the retinal prosthesis 180, and the electrode part 190. The retinal prosthesis system 300 is placed in the eye.

The Alvarez lens 110 is placed in the eye in place of the lens 26, and configured to be able to change at least the focal length. The transparent solar cell 130 is configured to transmit part of incident light therethrough and convert the energy of other part into electrical energy. The first detector 140 is configured to detect the movement of the ciliary body 27 or a biological signal for moving the ciliary body. Examples of the biological signal for moving the ciliary body include a signal sent from the brain to the ciliary body through the nerves. When the external power supply is required, the first detector 140 operates by receiving the electrical energy obtained by the transparent solar cell 130. The driver 150 is configured to operate with the electrical energy received from the transparent solar cell 130 and change the focal length of the Alvarez lens 110 based on the detection result obtained by the first detector 140. The controller 170 is configured to operate with the electrical energy received from the transparent solar cell 130 and control the driver 150. As a specific example, based on the detection result obtained by the first detector 140, the controller 170 generates a drive signal to indicate the change amount and change direction of the focal length according to the detection result, and controls the driver 150 by using the drive signal. The retinal prosthesis 180 is configured to operate with the electrical energy received from the transparent solar cell 130 and detect light having transmitted through the transparent solar cell 130 by a photoelectric conversion element array. The electrode part 190 is used to send an electrical signal generated by the retinal prosthesis 180 to the visual cortex of the brain.

A power supply line is provided between the transparent solar cell 130 and the first detector 140 to supply the electric power generated by the transparent solar cell 130. In addition, a power supply line is provided between the transparent solar cell 130 and the driver 150 to supply the electric power generated by the transparent solar cell 130. Further, a power supply line is provided between the transparent solar cell 130 and the controller 170 to supply the electric power generated by the transparent solar cell 130. Besides, a signal line is provided between the first detector 140 and the controller 170 to send the detection result obtained by the first detector 140. A signal line is provided between the controller 170 and the driver 150 to supply a drive signal for driving the driver 150. Otherwise, the retinal prosthesis system of FIG. 7 is the same as that of FIG. 1.

In this embodiment, the Alvarez lens 110 transmits light incident on the eye, and the transparent solar cell 130 converts the energy of the light having transmitted through the Alvarez lens 110 into electrical energy. That is, the Alvarez lens 110 is placed on the cornea side, while the transparent solar cell 130 is placed on the fundus side.

(Alvarez Lens, Driver)

The Alvarez lens 110 includes a pair of optical elements 111 and 112, and its spherical power can be changed by the relative movement of the optical elements 111 and 112. In other words, the Alvarez lens 110 is configured to have a focal length which can be changed by the relative movement of the optical elements 111 and 112.

Figure 8:
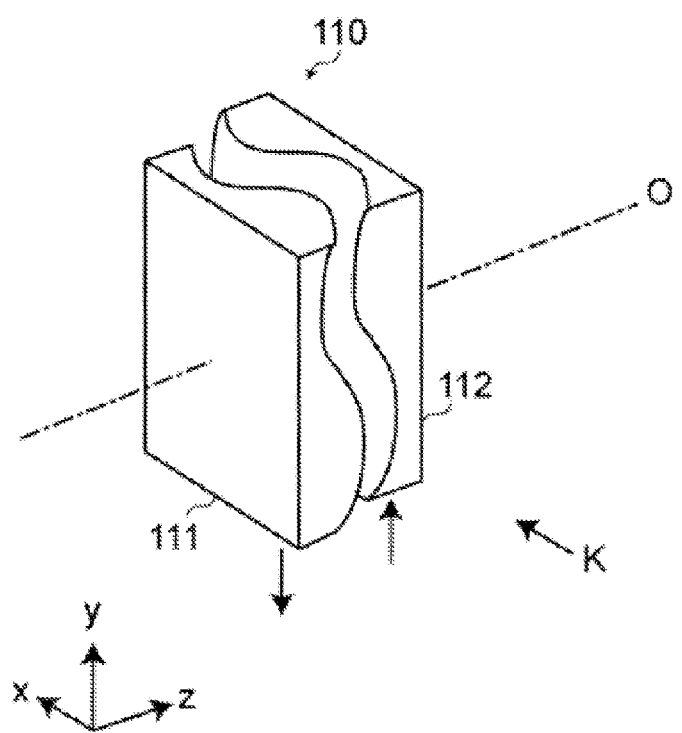
FIG. 8 is a schematic diagram illustrating an example of the configuration of a retinal prosthesis system according to an embodiment.

FIG. 8 is an explanatory diagram of the Alvarez lens 110 of the second embodiment. In FIG. 8, the horizontal direction is defined as x direction, the vertical direction is defined as y direction, and the fundus direction is defined as z direction. The optical elements 111 and 112 are placed on a predetermined axis O of the Alvarez lens 110. The optical elements 111 and 112 each have a known three-dimensional curved surface as a surface facing each other.

A direction parallel to the axis O is defined as the z direction. By relatively moving the optical elements 111 and 112 in the y direction (vertical direction) in the xy plane perpendicular to the axis O (see FIG. 8), the refracted power (spherical power) obtained by optically combining the optical elements 111 and 112 can be continuously changed. In FIG. 8, the optical element 111 is moved downward (−y direction), and the optical element 112 is moved upward (+y direction).

Figure 9:
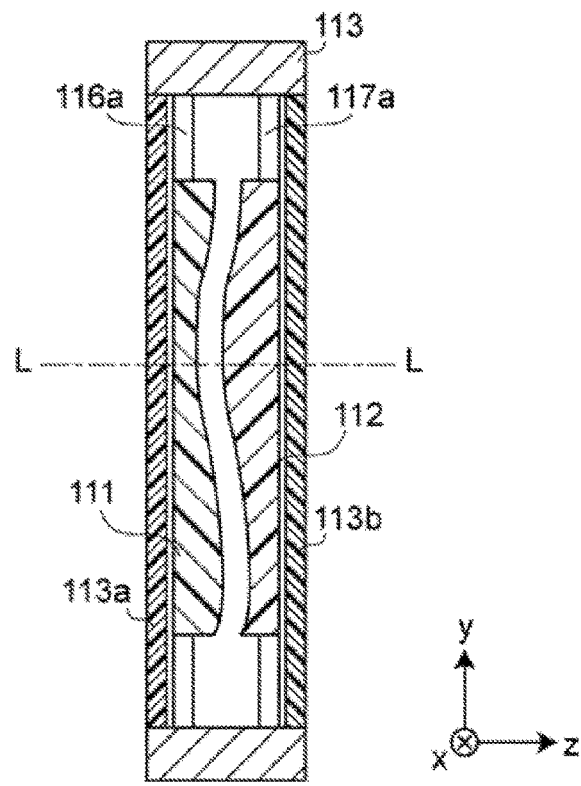
FIG. 9 is a schematic diagram illustrating an example of the configuration of a retinal prosthesis system according to an embodiment.
Figure 10:
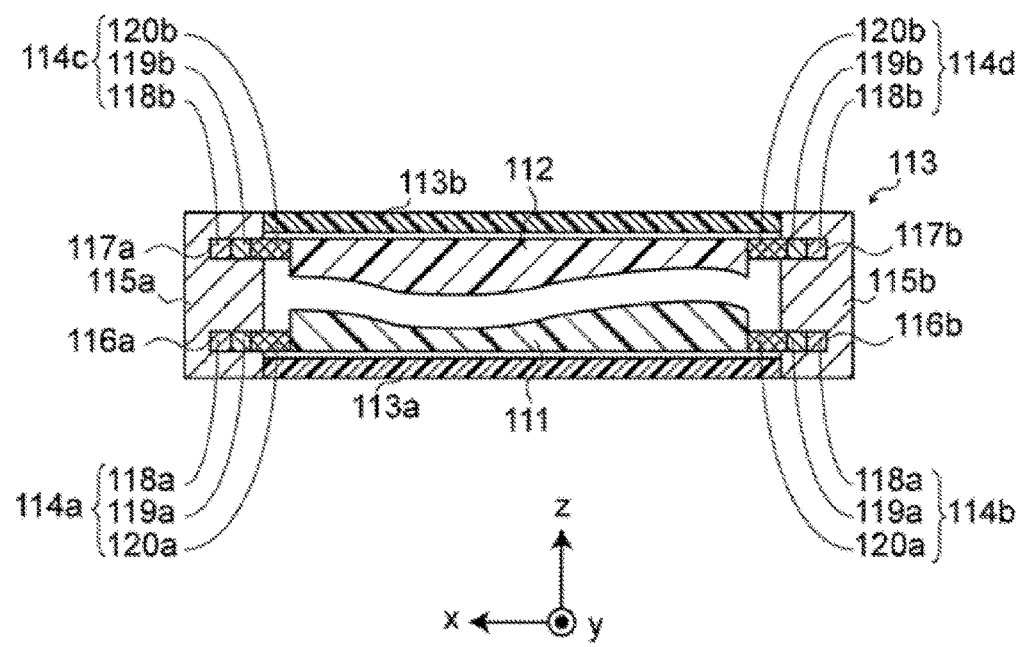
FIG. 10 is a schematic diagram illustrating an example of the configuration of a retinal prosthesis system according to an embodiment.

FIGS. 9 and 10 illustrate examples of cross-sections of the Alvarez lens 110 of the first embodiment. FIG. 9 is a schematic vertical cross-sectional view, passing through the axis O, of the Alvarez lens 110 of FIG. 8 as viewed from the K direction. FIG. 10 is a cross-sectional view taken along line L-L in FIG. 9.

The optical elements 111 and 112, which constitute the Alvarez lens 110, are housed in an envelope 113 filled with a medium such as air having a predetermined transmittance. This medium need not necessarily be air but may be a gas other than air, a liquid, or a solid having a viscosity. The envelope 113 is provided with a transparent member 113a that transmits the light from the first main surface side (outside) to the inside of the envelope 113, and a transparent member 113b that transmits the light inside the envelope 113 to the second main surface side (in the eye), which is opposite to the first main surface. The optical elements 111 and 112 are located between the transparent members 113a and 113b in the envelope 113.

Ultrasonic linear motors 114a to 114d are arranged inside the envelope 113. The ultrasonic linear motors 114a to 114d relatively move the optical elements 111 and 112 in the vertical direction (y direction in FIG. 8). In this embodiment, the ultrasonic linear motors 114a to 114d constitute the driver 150.

The envelope 113 is provided with side walls 115a and 115b on the left and right sides. The side wall 115a has guide grooves 116a and 117a formed to extend vertically. The side wall 115b has guide grooves 116b and 117b formed to extend vertically correspondingly to the vertical guide grooves 116a and 117a. The ultrasonic linear motor 114a is provided in the guide groove 116a. The ultrasonic linear motor 114b is provided in the guide groove 116b.

The ultrasonic linear motors 114a and 114b each include a piezoelectric element array 118a, a vibrator 119a as a stator, and a mover 120a. The piezoelectric element array 118a is formed, for example, in a straight line by connecting electrodes and piezoelectric elements alternately. The vibrator 119a includes, for example, a number of teeth arranged in the longitudinal direction on the opposite side to the piezoelectric element array 118a, and is driven to vibrate by the piezoelectric element array 118a. The mover 120a is engaged with the teeth of the vibrator 119a by friction. The piezoelectric element array 118a is fixed to the vibrator 119a. The movers 120a and 120a of the guide grooves 116a and 116b are fixed on both sides of the optical element 111.

Similarly, the ultrasonic linear motor 114c is provided in the guide groove 117a. The ultrasonic linear motor 114d is provided in the guide groove 117b.

The ultrasonic linear motors 114c and 114d each include a piezoelectric element array 118b, a vibrator 119b as a stator, and a mover 120b. The piezoelectric element array 118b is formed, for example, in a straight line by connecting electrodes and piezoelectric elements alternately. The vibrator 119a includes, for example, a number of teeth arranged in the longitudinal direction on the opposite side to the piezoelectric element array 118b, and is driven to vibrate by the piezoelectric element array 118b. The mover 120b is engaged with the teeth of the vibrator 119b by friction. The piezoelectric element array 118b is fixed to the vibrator 119b. The movers 120b and 120b of the guide grooves 117a and 117b are fixed on both sides of the optical element 112.

In the configuration illustrated in FIGS. 9 and 10, the voltage applied to the electrodes of the piezoelectric element array 118a is controlled to change the phase of bending standing-wave vibration generated on the teeth side of the vibrator 119a. Thereby, the vibrator 119a moves the mover 120a up or down. The ultrasonic linear motors 114a and 114b may have the structure of a known ultrasonic linear motor.

Similarly, the voltage applied to the electrodes of the piezoelectric element array 118b is controlled to change the phase of bending standing-wave vibration generated on the teeth side of the vibrator 119b. Thereby, the vibrator 119b moves the mover 120b up or down. The ultrasonic linear motors 114c and 114d may have the structure of a known ultrasonic linear motor.

With the above configuration, the ultrasonic linear motors 114a to 114d move the optical elements 111 and 112 vertically, and thereby the Alvarez lens 110 is set to have a desired spherical power. Incidentally, the Alvarez lens 110 having the structure described above may be sealed in a package of a predetermined shape so that it can be easily inserted in the eye and held therein. The Alvarez lens 110 is an example of the "lens". The driver 150 is an example of the "driver".

(First Detector)

The focal length of the eye is changed by changing the thickness of the lens enclosed within the lens capsule. The thickness of the lens varies depending on the movement of the ciliary body, which is transmitted to the lens capsule through the ciliary zonule (zonule of Zinn). The first detector 140 detects at least one of the acceleration of a predetermined portion of the ciliary body, the movement amount of a predetermined portion of the ciliary body, the tension of the ciliary zonule, and a myoelectric potential signal of the ciliary body, which change the thickness of the lens.

When used to detect an acceleration of a predetermined portion of the ciliary body, the first detector 140 includes an acceleration sensor or the like attached to the predetermined portion of the ciliary body. In this case, the first detector 140 outputs the detected acceleration to the controller 170. For example, the controller 170 is configured to output a drive signal having a predetermined relationship to the acceleration detected by the first detector 140. Thus, even if the movement of the ciliary body becomes insufficient due to its weakening, the controller 170 can output a drive signal obtained by amplifying the movement of the ciliary body. Besides, to respond to the characteristics of the eye where it is placed and further weakening of the ciliary body afterwards, for example, the controller 170 may refer to table information that associates the acceleration with a drive signal (amplitude and phase), and output a drive signal associated with the detected acceleration to the driver 150. In this case, the table information is variable.

When used to detect the movement amount of a predetermined portion of the ciliary body, the first detector 140 includes a position sensor or the like attached to the predetermined portion of the ciliary body. In this case, the first detector 140 outputs the detected movement amount to the controller 170. For example, the controller 170 is configured to output a drive signal having a predetermined relationship to the movement amount detected by the first detector 140. Thus, even if the movement of the ciliary body becomes insufficient due to its weakening, the controller 170 can output a drive signal obtained by amplifying the movement of the ciliary body. Besides, to respond to the characteristics of the eye where it is placed and further weakening of the ciliary body afterwards, for example, the controller 170 may refer to table information that associates the movement amount with a drive signal (amplitude and phase), and output a drive signal associated with the detected movement amount to the driver 150. In this case, the table information is variable.

When used to detect the tension of the ciliary zonule, the first detector 140 includes a tension sensor or the like attached to the ciliary zonule. In this case, the first detector 140 outputs the detected tension to the controller 170. For example, the controller 170 is configured to output a drive signal having a predetermined relationship to the tension detected by the first detector 140. Thus, even if the movement of the ciliary body becomes insufficient due to its weakening, the controller 170 can output a drive signal obtained by amplifying the movement of the ciliary body. Besides, to respond to the characteristics of the eye where it is placed and further weakening of the ciliary body afterwards, for example, the controller 170 may refer to table information that associates the tension with a drive signal (amplitude and phase), and output a drive signal associated with the detected tension to the driver 150. In this case, the table information is variable.

When used to detect a myoelectric potential signal (in a broader sense, a biological signal) of a predetermined portion of the ciliary body, the first detector 140 includes a myoelectric potential sensor or the like attached to the predetermined portion of the ciliary body. In this case, the first detector 140 outputs the detected myoelectric potential signal to the controller 170. For example, the controller 170 is configured to output a drive signal having a predetermined relationship to the myoelectric potential signal detected by the first detector 140. Thus, even if the movement of the ciliary body becomes insufficient due to its weakening, the controller 170 can output a drive signal obtained by amplifying the movement of the ciliary body. Besides, to respond to the characteristics of the eye where it is placed and further weakening of the ciliary body afterwards, for example, the controller 170 may refer to table information that associates the myoelectric potential signal with a drive signal (amplitude and phase), and output a drive signal associated with the detected myoelectric potential signal to the driver 150. In this case, the table information is variable.

The first detector 140 may be configured by using any one of the above sensors, or may be configured to output a drive signal corresponding to the combination of detection results obtained by at least two of the above sensors to the driver 150.

With the above configuration, the first detector 140 detects the movement of the ciliary body or a biological signal for moving the ciliary body, and outputs the detection result to the controller 170. The controller 170 generates a drive signal based on the detection result obtained by the first detector 140. Note that the first detector 140 may include a sensor that needs no power supply from the transparent solar cell 130. In this case, there is no need of the power supply line provided between the transparent solar cell 130 and the first detector 140. The first detector 140 is an example of the "first detector".

(Controller)

The controller 170 includes a central processing unit (CPU) and a memory that stores a program which is executed by the CPU. The controller 170 controls the driver 150 according to the program stored in the memory. Here, the controller 170 analyzes a detection result obtained by the first detector 140 or an image detected by the retinal prosthesis 180 to control the driver 150, thereby changing the focal length of the Alvarez lens 110. As described above, the controller 170 can output a drive signal obtained by amplifying the movement of the ciliary body to the driver 150. The driver 150 changes the focal length of the Alvarez lens 110 based on a drive signal corresponding to the detection result obtained by the first detector 140. Thereby, even if the movement of the ciliary body becomes insufficient due to its weakening, the focal length of the Alvarez lens 110 can be changed appropriately by the driver 150 driven under the control of the controller 170. The controller 170 may be implemented by an application-specific integrated circuit (ASIC) or a control circuit. The controller 170 is an example of the "controller".

[Arrangement Example]

Figure 11:
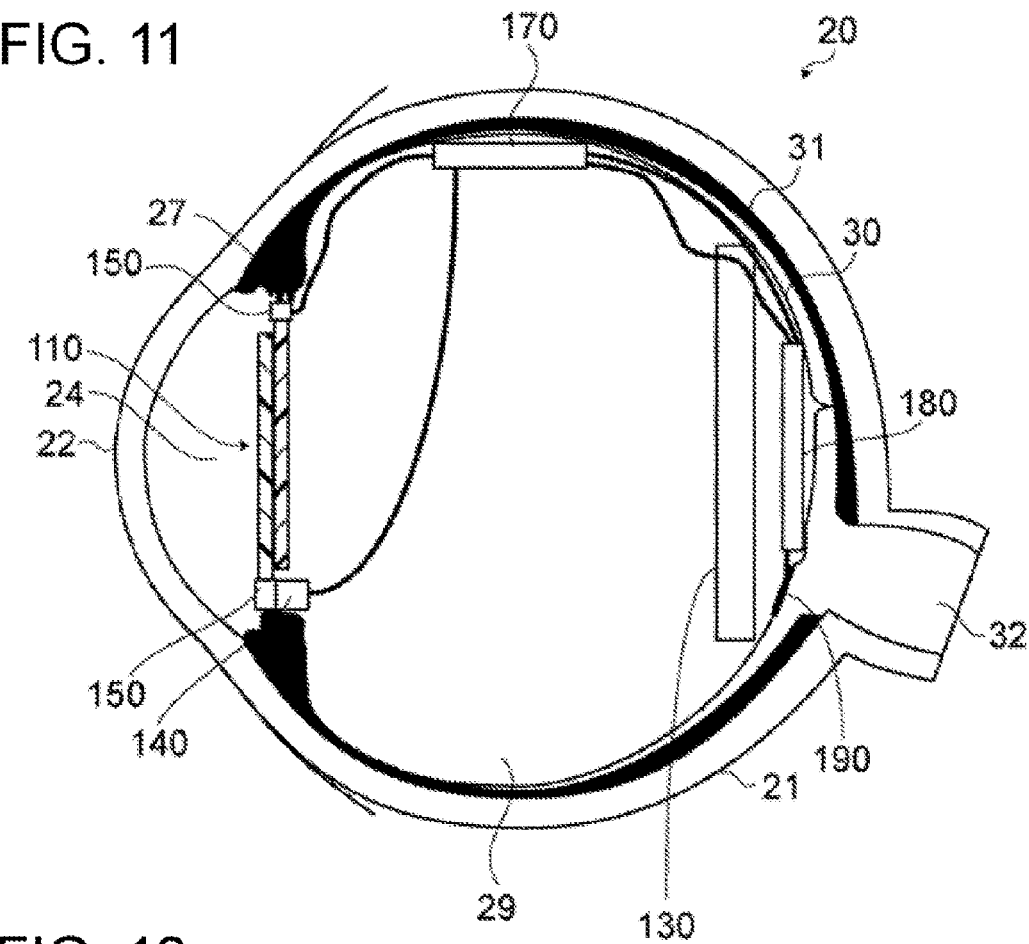
FIG. 11 is a schematic diagram illustrating an example of the configuration of a retinal prosthesis system according to an embodiment.

FIG. 11 is a schematic cross-sectional view of an eye in which the retinal prosthesis system 300 of the third embodiment is placed. Specifically, FIG. 11 is a cross-sectional view of the right eye as viewed from the above. Like reference numerals designate like parts as in FIG. 3 or 7, and the same description may not be repeated. For convenience of explanation, FIG. 11 may not illustrate power lines and signal lines provided between parts of the retinal prosthesis system 300.

The eye 20 has a substantially spherical shape and the outer is covered by the sclera 21. The light incident from the front of the eye 20 is refracted by the cornea 22, and is refracted again by the Alvarez lens 110 placed at the position of the lens.

The first detector 140 can detect the movement of the ciliary body 27 or a biological signal for moving the ciliary body 27. The detection result obtained by the first detector 140 is sent to the controller 170. The controller 170 generates a drive signal based on the detection result obtained by the first detector 140, and outputs the drive signal to the driver 150. The driver 150 drives the Alvarez lens 110 based on the drive signal received from the controller 170. Thus, the focal length of the Alvarez lens 110 is changed.

After having been refracted by the retinal prosthesis system 300 with the focal length changed in this manner, the light passes through the vitreous body 29 and transmits through the transparent solar cell 130. At this time, the transparent solar cell 130 converts the energy of part of the incident light into electrical energy. The electrical energy obtained by the transparent solar cell 130 is supplied to the first detector 140, the driver 150, the controller 170, and the retinal prosthesis 180.

The light having transmitted through the transparent solar cell 130 reaches the retinal prosthesis 180. The photoelectric conversion element array of the retinal prosthesis 180 converts the light into an electrical signal. The electrical signal generated by the retinal prosthesis 180 is transmitted through the electrode part 190 to the photoreceptor cells, the retinal ganglion cells, the bipolar cells, or the optic nerve.

[Operation]

Figure 12:
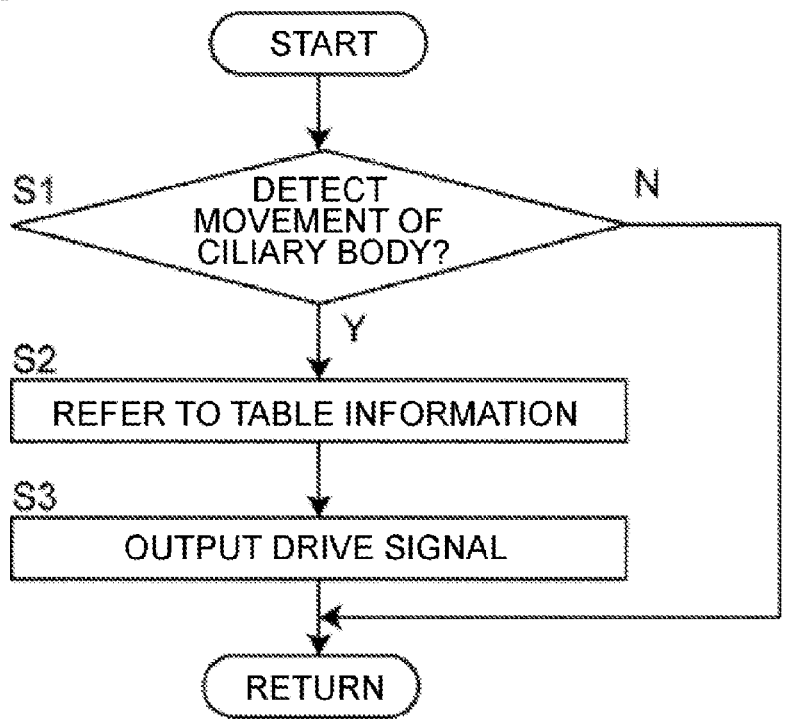
FIG. 12 is a flowchart illustrating an example of the operation of the retinal prosthesis system of the embodiment.

FIG. 12 is a flowchart of an example of the operation of the retinal prosthesis system 300 of the third embodiment. The memory of the controller 170 stores programs each corresponding to a step in FIG. 12. The CPU of the controller 170 reads the program from the memory, and executes it to perform a corresponding process.

(S1: Detect Movement of Ciliary Body?)

First, the controller 170 monitors whether the first detector 140 has detected the movement of the ciliary body 27 based on the detection result obtained by the first detector 140. When the first detector 140 has not detected the movement of the ciliary body 27 (step S1: N), the controller 170 continues to monitor the detection of the movement of the ciliary body 27 by the first detector 140 (Return). On the other hand, when the first detector 140 has detected the movement of the ciliary body 27 (step S1: Y), the controller 170 controls the operation of the retinal prosthesis system 300 such that the process moves to step S2. Incidentally, in step S1, the controller 170 may monitor whether the first detector 140 has detected a biological signal for moving the ciliary body 27.

(S12: Refer to Table Information)

Table information is set in advance in which values of physical quantities detected by the first detector 140 are each associated with the content (amplitude or phase) of a drive signal. As a specific example, when the first detector 140 detects the physical quantity of any one of the acceleration of a predetermined portion of the ciliary body 27, the movement amount of a predetermined portion of the ciliary body 27, the tension of the ciliary zonule 28, and a myoelectric potential signal of the ciliary body 27, table information is set in advance in which the value of the physical quantity is associated with the content of a drive signal.

Besides, when the first detector 140 detects the physical quantities of two or more of the acceleration of a predetermined portion of the ciliary body 27, the movement amount of a predetermined portion of the ciliary body 27, the tension of the ciliary zonule 28, and a myoelectric potential signal of the ciliary body 27, table information is set in advance in which a combination of the values of the physical quantities is associated with the content of a drive signal. The controller 170 refers to any table information as described above to generate a drive signal for changing the focal length of the Alvarez lens 110. For example, the controller 170 generates a drive signal based on the content of the drive signal set in the table information according to the detection result obtained by the first detector 140.

(S3: Output Drive Signal)

The controller 170 outputs, to the driver 150, the drive signal generated with reference to the table information in step S2. Thereafter, the controller 170 controls the operation of the retinal prosthesis system 300 such that the process moves to step S1 (Return).

In this embodiment, when the first detector 140 has detected the movement of the ciliary body 27 (or a biological signal for moving the ciliary body 27) that increases the thickness of the lens, in the retinal prosthesis system 300, the Alvarez lens 110 is driven to reduce the current focal length based on the content of the table information set as described above. On the other hand, when the first detector 140 has detected the movement of the ciliary body 27 (or a biological signal for moving the ciliary body 27) that reduces the thickness of the lens, in the retinal prosthesis system 300, the Alvarez lens 110 is driven to increase the current focal length based on the content of the table information set as described above.

Incidentally, in addition to the first detector 140, there may be provided a means for detecting the eye movement. In this case, based on the detection results obtained by the first detector 140 and the means, the controller 170 cancels information on the eye movement from the detection result obtained by the first detector 140 to thereby extract substantial information required to change the thickness of the lens.

Further, in this embodiment, the transparent solar cell 130 may be placed on the cornea side, and the Alvarez lens 110 may be placed on the fundus side. In this case, the Alvarez lens 110 is located between the transparent solar cell 130 and the retinal prosthesis 180.

[Effects]

The retinal prosthesis system 300 is an example of the retinal prosthesis system of this embodiment. Described below are the effects of the retinal prosthesis system of this embodiment.

The retinal prosthesis system (e.g., the retinal prosthesis system 300) may further include a lens (e.g., the Alvarez lens 110) and a driver (e.g., the driver 150) configured to drive the lens. That is, the retinal prosthesis system may include a lens, a converter (e.g., the transparent solar cell 130), a driver, a retinal prosthesis (e.g., the retinal prosthesis 180), and a transmitter (e.g., the electrode part 190).

The lens is placed in the eye, and configured to allow changes of the focal length. The converter is placed in the eye, and configured to transmit part of light incident on the eye therethrough and convert the energy of other part of the light into electrical energy. Here, "other part of the light" may include the entire part of the light incident on the eye excluding the part of the light that transmits through the converter. The driver is placed in the eye, and configured to operate with the electrical energy received from the converter to change the focal length of the lens. The retinal prosthesis is placed in the eye, and includes a photoelectric conversion element array configured to operate with the electrical energy received from the converter to detect the light having transmitted through the converter to generate an electrical signal. The transmitter is used to send the electrical signal generated by the retinal prosthesis to the visual cortex of the brain.

In the retinal prosthesis system, the converter converts the energy of light incident on the eye into electrical energy. The driver receives the electrical energy from the converter to drive the lens. Thereby, in the eye, the converter can be placed on the cornea side with respect to the retinal prosthesis placed near the fundus. That is, a configuration can be implemented in which the converter and the retinal prosthesis are located on the axis of light incident on the eye. Accordingly, the converter and the retinal prosthesis do not limit their sizes each other. As the space in the eye can be effectively utilized, both a space for the placement of the retinal prosthesis in a desired size and a space for converting the energy of light into electrical energy can be ensured in the eye. Moreover, the lens can be placed in the eye in a conventional manner. Further, the focal length of the lens can be changed appropriately by using the energy of light incident on the eye, and the retinal prosthesis is capable of generating an electrical signal by receiving the light having transmitted through the lens.

In addition, the retinal prosthesis system may include a first detector (e.g., the first detector 140) configured to be placed in the eye, and detect the movement of the ciliary body or a biological signal for moving the ciliary body. The driver changes the focal length of the lens based on the detection result obtained by the first detector.

With the retinal prosthesis system, since the first detector detects the movement of the ciliary body or a biological signal for moving the ciliary body, the driver can change the focal length of the lens by amplifying the movement of the ciliary body. Thus, even if the movement of the ciliary body is insufficient, the focal length of the lens can be changed appropriately by amplifying the movement of the ciliary body.

In the retinal prosthesis system, the first detector may be configured to detect at least one of the acceleration of a predetermined portion of the ciliary body, the movement amount of a predetermined portion of the ciliary body, the tension of the ciliary zonule, and a myoelectric potential signal of a predetermined portion of the ciliary body.

The movement of the ciliary body leads to a change in the acceleration of the predetermined portion of the ciliary body, the movement amount of the predetermined portion of the ciliary body, the tension of the ciliary zonule, or the myoelectric potential signal of the predetermined portion of the ciliary body. Therefore, the first detector is provided to detect such physical quantities. Thereby, the movement of the ciliary body can be detected with high accuracy. Thus, the lens can be controlled to be driven with high accuracy according to the movement of the ciliary body.

In addition, the retinal prosthesis system may include a controller (e.g., the controller 170). In this case, the controller is configured to operate with the electrical energy received from the converter and control the driver.

With the retinal prosthesis system provided with the controller that operates with the electrical energy obtained by the converter, the driver can be controlled more finely. Thus, the focal length of the lens can be changed more appropriately.

In the retinal prosthesis system, the converter may include a transparent solar cell configured to transmit part of light incident on the eye and convert the energy of other part into electrical energy.

The transparent solar cell transmits light incident on the eye. The light having transmitted through the transparent solar cell reaches the retinal prosthesis. With this, it becomes possible to secure the size of the light receiving surface of the transparent solar cell without blocking the light to reach the retinal prosthesis. Moreover, both a space for the placement of the retinal prosthesis in a desired size and a space for converting the energy of light into electrical energy can also be ensured. Further, it is possible to suppress a decrease in the light absorption efficiency of the retinal prosthesis. Thereby, more information can be transmitted through the optic nerve.

In the retinal prosthesis system, the lens is desirably configured to allow a continuous change of the focal length. With the retinal prosthesis system, the focal length can be finely changed according to the movement of the ciliary body or the like. The lens may be configured to allow the change of the focal length at each step that can be set afterwards.

In the retinal prosthesis system, the lens may include an Alvarez lens.

With the retinal prosthesis system, the focal length can be changed with the use of the Alvarez lens by using power generated in the eye.

<Fourth Embodiment>

According to a fourth embodiment, the Alvarez lens 110 is driven based on an image detected by the retinal prosthesis 180. In the following, a retinal prosthesis system according to the fourth embodiment is described focusing on differences from the third embodiment.

[Configuration]

The retinal prosthesis system of the fourth embodiment has basically the same configuration as the retinal prosthesis system 300 of the third embodiment. The retinal prosthesis system of the fourth embodiment is described below with reference to FIG. 7 or 11.

[Operation]

Figure 13:
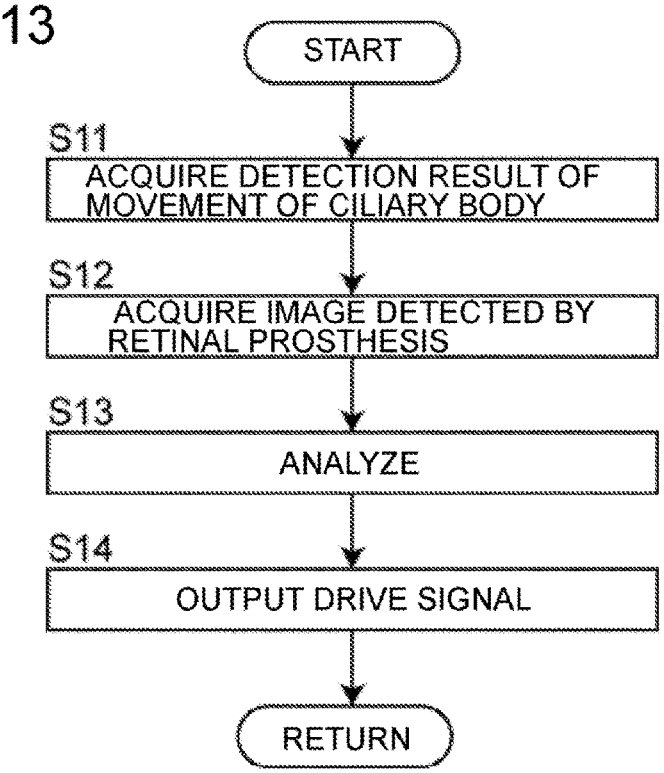
FIG. 13 is a flowchart illustrating an example of the operation of the retinal prosthesis system of the embodiment.

FIG. 13 is a flowchart of an example of the operation of the retinal prosthesis system of the fourth embodiment. The memory of the controller 170 stores programs each corresponding to a step in FIG. 13. The CPU of the controller 170 reads the program from the memory, and executes it to perform a corresponding process.

(S11: Acquire Detection Result of Movement of Ciliary Body)

First, the controller 170 acquires a detection result of the movement of the ciliary body 27 obtained by the first detector 140. The detection result includes the detection result of the physical quantity of at least one of the acceleration of a predetermined portion of the ciliary body 27, the movement amount of a predetermined portion of the ciliary body 27, the tension of the ciliary zonule 28, and a myoelectric potential signal of the ciliary body 27.

(S12: Acquire Image Detected by Retinal Prosthesis)

Next, the controller 170 acquires an image detected by the retinal prosthesis 180. As a specific example, the controller 170 acquires an electrical signal generated by each of the photoelectric conversion elements in the retinal prosthesis 180.

(S13: Analyze)

Next, the controller 170 analyzes at least one of the detection result obtained in step S11 and the image acquired in step S12. The controller 170 generates a drive signal to drive the driver 150 based on the analysis result.

For example, the controller 170 generates a drive signal corresponding to the detection result obtained by the first detector 140. As a specific example, the controller 170 determines whether the movement of the ciliary body 27 is a movement for thickening the lens or a movement for thinning the lens based on the detection result obtained by the first detector 140. The controller 170 generates a drive signal based on the determination result. Upon detection of the movement of the ciliary body for thickening the lens, the controller 170 generates a drive signal to reduce the current focal length of the Alvarez lens 110. Upon detection of the movement of the ciliary body for thinning the lens, the controller 170 generates a drive signal to increase the current focal length of the Alvarez lens 110. At this time, the controller 170 may generate the drive signal so as to amplify the movement of the ciliary body 27. For example, when the first detector 140 detects a very small amount of movement of the ciliary body 27, the controller 170 multiplies the small amount of movement by an amplification factor corresponding to the amount of the movement to generate the drive signal. The focal length of the Alvarez lens 110 is changed based on the drive signal thus generated. The amplification factor corresponding to the amount of the movement can be changed afterwards. The drive signal is a signal corresponding to the amount and direction of the change of the focal length.

For example, the controller 170 generates a drive signal corresponding to the sharpness of the image obtained by the retinal prosthesis 180. As a specific example of this case, the controller 170 detects lines in an image obtained by the retinal prosthesis 180. The controller 170 generates a drive signal to change the focal length for each first step in a direction in which the harmonic components of the boundary of the lines detected are emphasized. The controller 170 also detects the edge of the image obtained by the retinal prosthesis 180. The controller 170 generates a drive signal to change the focal length for each second step in a direction in which the harmonic components of the edge detected are emphasized. Further, the controller 170 detects the contrast of the image obtained by the retinal prosthesis 180. The controller 170 generates a drive signal to change the focal length for each third step in a direction in which the contrast of the image is the maximum.

For another example, the controller 170 may generate a drive signal based on the detection result obtained by the first detector 140 and the image obtained by the retinal prosthesis 180. As a specific example of this case, when the movement of the ciliary body 27 is a movement for thickening the lens, the controller 170 generates a drive signal to reduce the current focal length of the Alvarez lens 110 for each fourth step in a direction in which the harmonic components of the boundary of the lines and the edge in the image are emphasized. Each of the first to the fourth steps can be changed afterwards.

(S14: Output Drive Signal)

The controller 170 outputs the drive signal generated in step S23 to the driver 150. Thereafter, the controller 170 controls the operation of the retinal prosthesis system such that the process moves to step S11 (Return).

[Effects]

The above retinal prosthesis system is an example of the retinal prosthesis system of this embodiment. In addition to the effects of the third embodiment, the retinal prosthesis system of this embodiment has the following advantages.

In the retinal prosthesis system, the controller may control the driver based on an electrical signal generated by the retinal prosthesis.

The electrical signal generated by the retinal prosthesis corresponds to an image detected by the retinal prosthesis. The controller may control the driver based on, for example, the sharpness, information on the edge, and the contrast of the image obtained by the retinal prosthesis. With the retinal prosthesis system, the focal length of the lens can be changed based on the electrical signal generated by the retinal prosthesis. Thus, even if it is not sufficient just to detect the movement of the ciliary body, the focal length of the lens can be changed more appropriately.

<Fifth Embodiment>

In the retinal prosthesis system of the above embodiments, the focal length of the Alvarez lens 110 may be changed according to the orientation of the eye (viewing direction, eye axis direction, visual axis direction). A retinal prosthesis system of a fifth embodiment has basically the same configuration as that of the third embodiment except the presence of a second detector to change the focal length of the Alvarez lens 110 according to the orientation of the eye. In the following, the retinal prosthesis system of the fifth embodiment is described focusing on differences from the third embodiment.

[Configuration]

Figure 14:
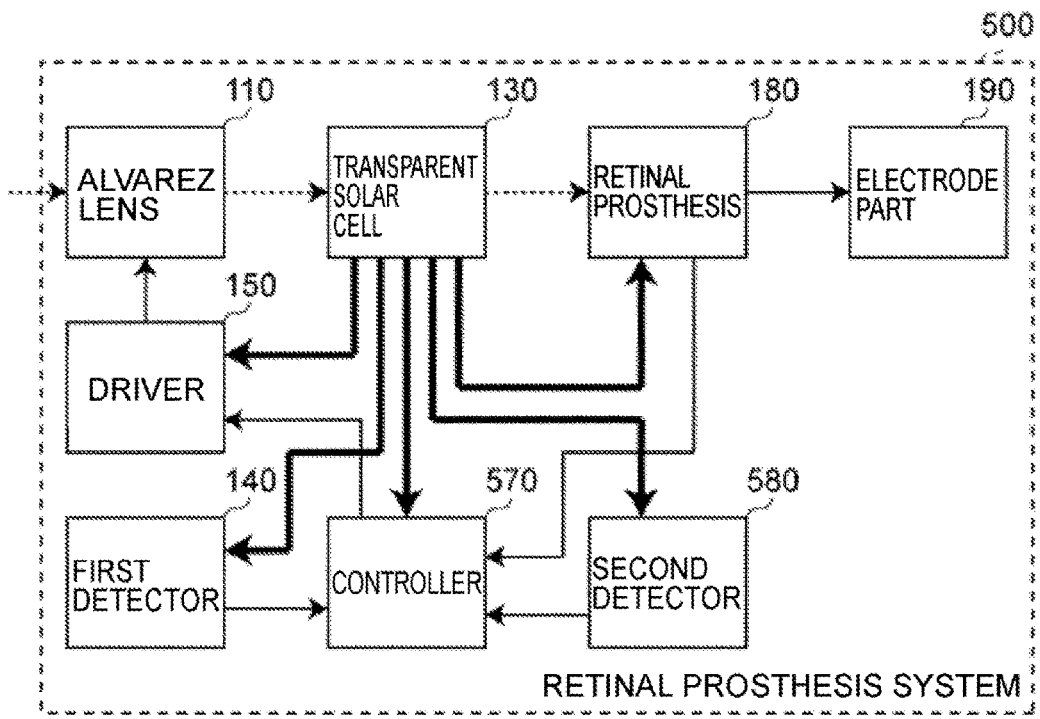
FIG. 14 is a schematic diagram illustrating an example of the configuration of a retinal prosthesis system according to an embodiment.

FIG. 14 is a functional block diagram illustrating an example of the configuration of a retinal prosthesis system according to the fifth embodiment. In FIG. 14, like reference numerals designate like parts as in FIG. 7, and the same description may not be repeated. In FIG. 14, the path of light is indicated by a broken arrow in distinction from the paths of others (e.g., electrical signal, etc.) each indicated by a solid line. A retinal prosthesis system 500 includes the Alvarez lens 110, the transparent solar cell 130, the first detector 140, the driver 150, the retinal prosthesis 180, the electrode part 190, a controller 570, and a second detector 580. The retinal prosthesis system 500 is placed in the eye.

The retinal prosthesis system 500 of the fifth embodiment is different from the retinal prosthesis system 300 of the third embodiment in the presence of the second detector 580 and the controller 570 in place of the controller 170.

A power supply line is provided between the transparent solar cell 130 and the controller 570 to supply the electric power generated by the transparent solar cell 130. In addition, a power supply line is provided between the transparent solar cell 130 and the second detector 580 to supply the electric power generated by the transparent solar cell 130. Besides, a signal line is provided between the first detector 140 and the controller 170 to send the detection result obtained by the first detector 140. A signal line is provided between the controller 170 and the driver 150 to supply a drive signal for driving the driver 150. Further, a signal line is provided between the controller 570 and the second detector 580 to send the detection result obtained by the second detector 580.

(Controller)

The controller 570 has basically the same configuration as the controller 170. The controller 570 may generate a drive signal for driving the driver 150 based on the detection result obtained by the second detector 580 in addition to the detection result obtained by the first detector 140. The controller 570 is an example of the "controller".

(Second Detector)

The second detector 580 operates with the electrical energy obtained by the transparent solar cell 130, and detects the orientation of the eye where the retinal prosthesis system 500 is located. The second detector 580 includes a tilt sensor attached to a predetermined portion of the eye (inside of the eye (the retina, etc.)) to detect the orientation of the eye. The tilt sensor is configured to detect an angle of inclination corresponding to the change amount of electrostatic capacitance when it is inclined, for example, with respect to the vertical direction using the electrostatic capacitance when it is held horizontally as a reference. The tilt sensor can also detect inclination in other directions, such as left and right directions. The orientation of the eye is specified by, for example, the detection result obtained by the tilt sensor that detects a vertical tilt. In addition, the orientation of the eye may be specified by detection results obtained by a plurality of tilt sensors each detecting an inclination in one of the two axial directions or three axial directions, which are perpendicular to one another and include the vertical direction. The detection result obtained by the second detector 580 is sent to the controller 570. The second detector 580 is an example of the "second detector".

[Arrangement Example]

Figure 15:
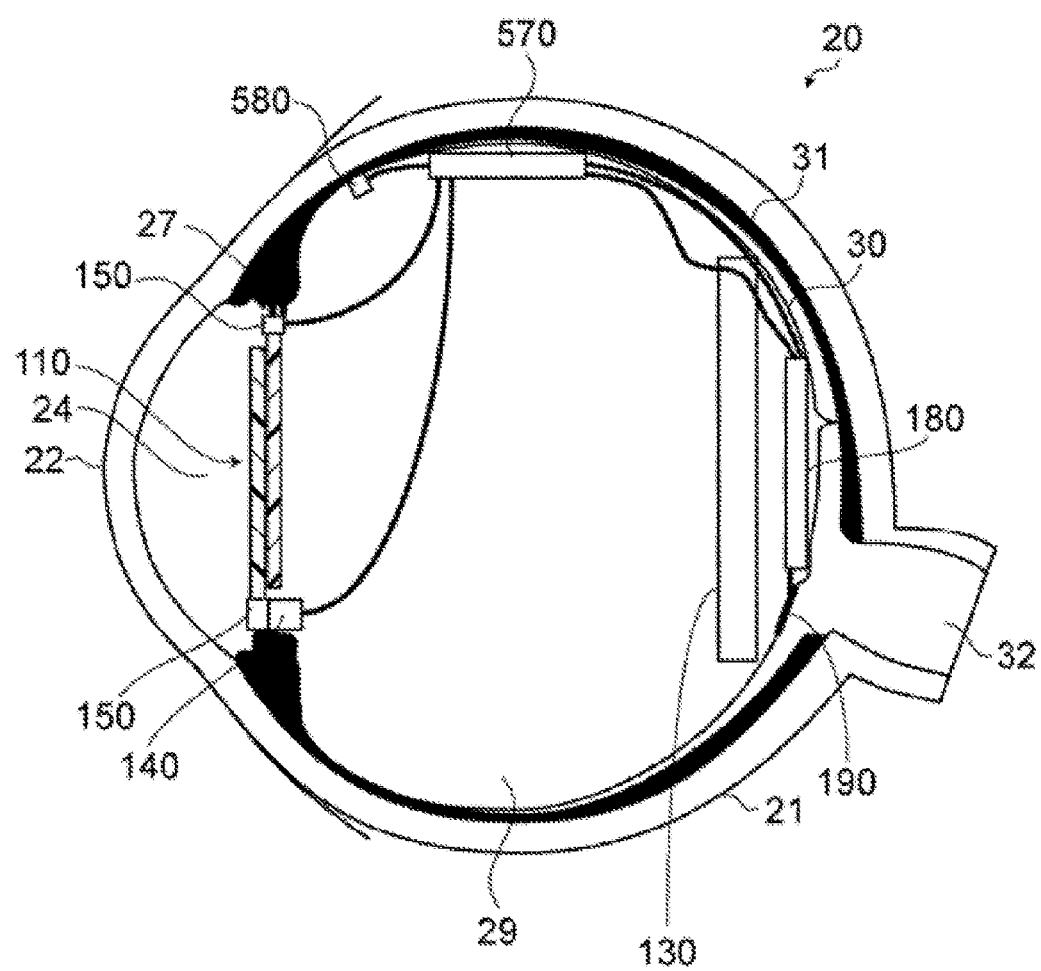
FIG. 15 is a schematic diagram illustrating an example of the configuration of a retinal prosthesis system according to an embodiment.

FIG. 15 is a schematic cross-sectional view of an eye in which the retinal prosthesis system 500 of the fifth embodiment is placed. FIG. 15 is a cross sectional view of the right eye as viewed from the above. Like reference numerals designate like parts as in FIGS. 11 and 14, and the same description may not be repeated. For convenience of explanation, FIG. 15 may not illustrate power lines and signal lines provided between parts of the retinal prosthesis system 500.

The eye 20 has a substantially spherical shape and the outer is covered by the sclera 21. The light incident from the front of the eye 20 is refracted by the cornea 22, and is refracted again by the Alvarez lens 110 placed at the position of the lens.

The controller 570 generates a drive signal based on at least one of the detection result obtained by the first detector 140 and the detection result obtained by the second detector 580, and outputs the drive signal to the driver 150. The driver 150 drives the Alvarez lens 110 based on the drive signal received from the controller 570. Thus, the focal length of the Alvarez lens 110 is changed.

After having been refracted by the retinal prosthesis system 500 with the focal length changed in this manner, the light passes through the vitreous body 29 and transmits through the transparent solar cell 130. At this time, the transparent solar cell 130 converts the energy of part of the incident light into electrical energy. The electrical energy generated by the transparent solar cell 130 is supplied to the first detector 140, the driver 150, the retinal prosthesis 180, the controller 570, and the second detector 580.

The light having transmitted through the transparent solar cell 130 reaches the retinal prosthesis 180. The photoelectric conversion element array of the retinal prosthesis 180 converts the light into an electrical signal. The electrical signal generated by the retinal prosthesis 180 is transmitted through the electrode part 190 to the photoreceptor cells, the retinal ganglion cells, the bipolar cells, or the optic nerve.

[Operation]

Figure 16:
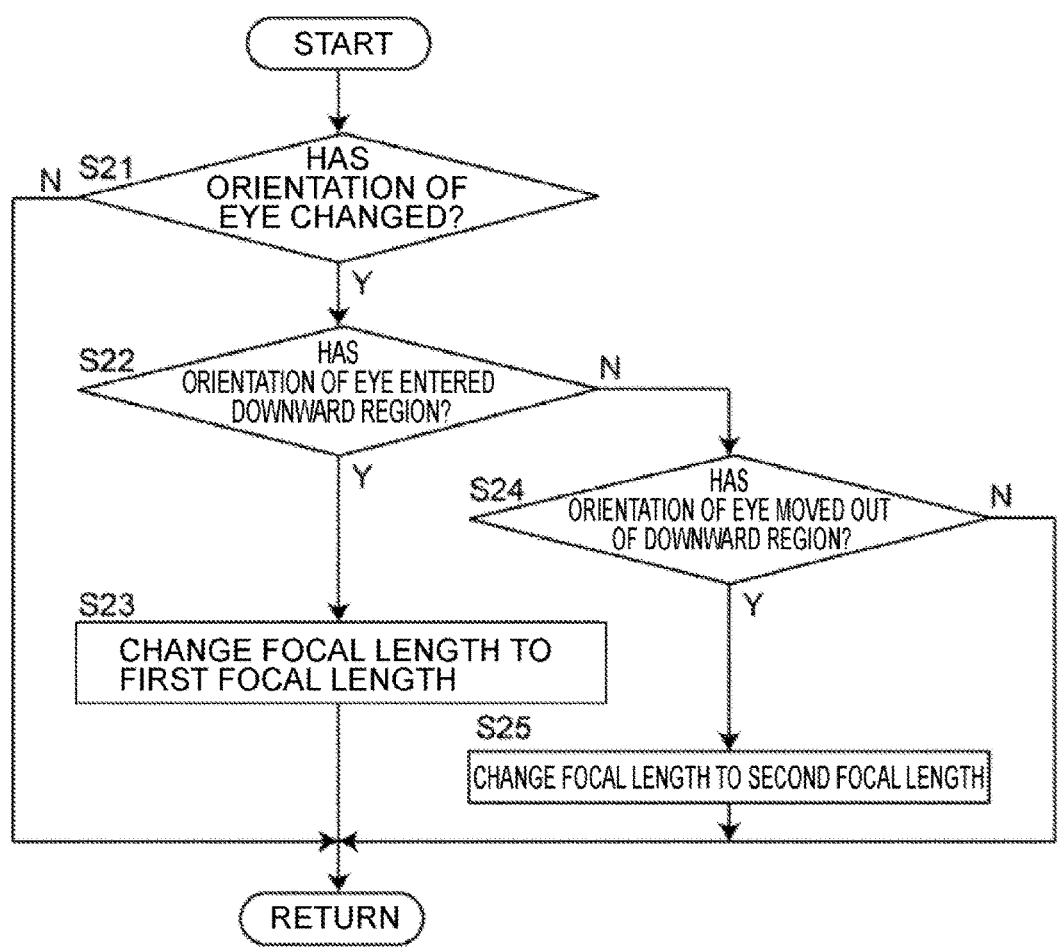
FIG. 16 is a flowchart illustrating an example of the operation of the retinal prosthesis system of the embodiment.

FIG. 16 is a flowchart of an example of the operation of the retinal prosthesis system 500 of the fifth embodiment. The memory of the controller 570 stores programs each corresponding to a step in FIG. 16. The CPU of the controller 570 reads the program from the memory, and executes it to perform a corresponding process.

(S21: Has Orientation of Eye Changed?)

First, the controller 570 monitors whether the orientation of the eye 20 has changed based on the detection result obtained by the second detector 580. Having detected no change in the orientation of the eye based on the detection result obtained by the second detector 580 (step S21: N), the controller 570 continues to monitor the detection of a change in the orientation of the eye 20 by the second detector 580 (Return). On the other hand, when the second detector 580 has detected a change in the orientation of the eye 20 (step S21: Y), the controller 170 controls the operation of the retinal prosthesis system 500 such that the process moves to step S22.

(S22: Has Orientation of Eye Entered Downward Region?)

When the second detector 580 has detected a change in the orientation of the eye 20, the controller 570 determines whether the orientation of the eye 20 has entered from the front direction into a downward region located below based on the detection result obtained by the second detector 580. Having determined that the orientation of the eye 20 has entered the downward region (step S22: Y), the controller 570 controls the operation of the retinal prosthesis system 500 such that the process moves to step S23. On the other hand, having determined that the orientation of the eye 20 has not entered the downward region (step S22: N), the controller 570 controls the operation of the retinal prosthesis system 500 such that the process moves to step S24.

(S23: Change Focal Length to First Focal Length)

Having determined that the orientation of the eye 20 has changed to downward based on the detection result obtained by the second detector 580, the controller 570 generates a drive signal to set the focal length of the Alvarez lens 110 to a first focal length that is shorter than the current focal length, and outputs the drive signal to the driver 150.

(S24: Has Orientation of Eye Moved Out of Downward Region?)

When the second detector 580 has not detected that the orientation of the eye 20 has entered the downward region, the controller 570 determines whether the orientation of the eye 20 has moved out of the downward region based on the detection result obtained by the second detector 580. Having determined that the orientation of the eye 20 has moved out of the downward region (step S24: Y), the controller 570 controls the operation of the retinal prosthesis system 500 such that the process moves to step S25. On the other hand, having determined that the orientation of the eye 20 has not moved out of the downward region (step S24: N), the controller 570 controls the operation of the retinal prosthesis system 500 such that the process moves to step S21 (Return).

(S25: Change Focal Length to Second Focal Length)

Having determined that the orientation of the eye 20 has moved out of the downward region based on the detection result obtained by the second detector 580, the controller 570 generates a drive signal to set the focal length of the Alvarez lens 110 to a second focal length that is longer than the current focal length. The second focal length is longer than the first focal length. The controller 570 outputs the drive signal to the driver 150.

After step S23 or step S25, the controller 570 controls the operation of the retinal prosthesis system 500 such that the process loops back to step S21 (Return).

As described above, when the second detector 580 has detected that the eye 20 is directed downward, the controller 570 can change the focal length of the Alvarez lens 110 to the first focal length that is shorter than the current focal length. Otherwise, the controller 570 can change the focal length of the Alvarez lens 110 to the second focal that is longer than the current focal length. Here, the second focal length is longer than the first focal length.

Although this embodiment describes an example in which the second detector 580 detects the orientation of the eye, and the focal length of the Alvarez lens 110 is changed according to the orientation of the eye, this is not a limitation.

The second detector 580 may detect convergence eye movement (convergence). The convergence eye movement is the movement of the left and right eyes turning inward (towards the nose) to see a nearby object. In this case, the controller 570 changes the focal length of the Alvarez lens 110 based on the detection result obtained by the second detector 580. As a specific example, when the second detector 580 has detected that the eye 20 is in a first convergence state, the controller 570 changes the focal length of the Alvarez lens 110 to a third focal length. The first convergence state is a state where the eyes are directed inside from a predetermined direction (e.g., the front direction). Incidentally, in addition to the second detector 580, there may be provided a means for detecting the convergence eye movement of the other eye. In this case, the controller 570 can determine whether the eyes have moved to simply change the viewing direction to the diagonal direction (the left and right eyes both turn in the same direction), for example, or the convergence eye movement has occurred (the left and right eyes both turn inside) based on the detection result obtained by the second detector 580 and the detection result obtained by the means.

Further, although this embodiment describes an example in which the orientation of the eye is detected by the second detector 580, which is added to the configuration of the third embodiment, this is not a limitation. The controller 170 of the third embodiment may be configured to analyze, for example, an image detected by the retinal prosthesis 180 (an electrical signal generated by the retinal prosthesis) to determine the orientation of the eye. As a specific example, the controller 170 obtains a change (direction, amount) in the orientation of the eye based on the change of an image in a predetermined area (e.g., central area including the center) of the image detected by the retinal prosthesis 180. In addition, the controller 170 obtains a change in the orientation of the eye based on a change in the position of a target image in the image detected by the retinal prosthesis 180. In this case, having determined that the eyes are directed downward based on the image detected by the retinal prosthesis 180 (an electrical signal generated by the retinal prosthesis), the controller 170 changes the focal length of the Alvarez lens 110 to a fifth focal length that is shorter than the current focal length.

[Effects]

The retinal prosthesis system 500 is an example of the retinal prosthesis system of this embodiment. In addition to the effects of the third embodiment or the fourth embodiment, the retinal prosthesis system of this embodiment has the following advantages.

The retinal prosthesis system (e.g., the retinal prosthesis system 500) may include a second detector (e.g., the second detector 580) configured to be placed in the eye to detect the orientation of the eye. In this case, the second detector operates with the electrical energy received from the converter. The controller controls the driver based on the detection result obtained by the second detector.

With the retinal prosthesis system, the orientation of the eye is detected in the eye so that the focal length of the lens can be changed depending on the orientation of the eye detected. Thus, when it can be specified whether to increase or reduce the focal length according to the orientation of the eye, the focal length of the lens can be changed based on the orientation of the eye detected.

In the retinal prosthesis system, when the second detector has detected that the eye is directed downward, the controller may change the focal length of the lens to a first focal length. Otherwise, the controller may change the focal length of the lens to a second focal length that is longer than the first focal length.

To see a nearby object (e.g., during reading, etc.), the eyes are generally pointed downward. Therefore, when the second detector has detected that the eyes are directed downward, the controller controls the lens to have the first focal length. Otherwise, the controller controls the lens to have the second focal length that is longer than the first focal length. Thus, the focal length of the lens can be changed appropriately according to the natural movement of the eyes.

In the retinal prosthesis system, the second detector may detect at least one of the acceleration of a predetermined portion of the eye and the convergence eye movement.

To see a nearby object, there is a change in the acceleration of a predetermined portion of the eye, or the convergence eye movement occurs. Therefore, the second detector is provided to detect such a movement. Thereby, a movement to see a nearby object can be detected with high accuracy. Thus, the lens can be controlled to be driven with high accuracy according to the movement of the eye.

<Sixth Embodiment>

In the third embodiment, the converter for converting light energy into electrical energy is described as being transmissive by way of example. However, the converter may be non-transmissive as in the second embodiment. In the following, a retinal prosthesis system according to a sixth embodiment is described focusing on differences from the third embodiment.

[Configuration]

Figure 17:
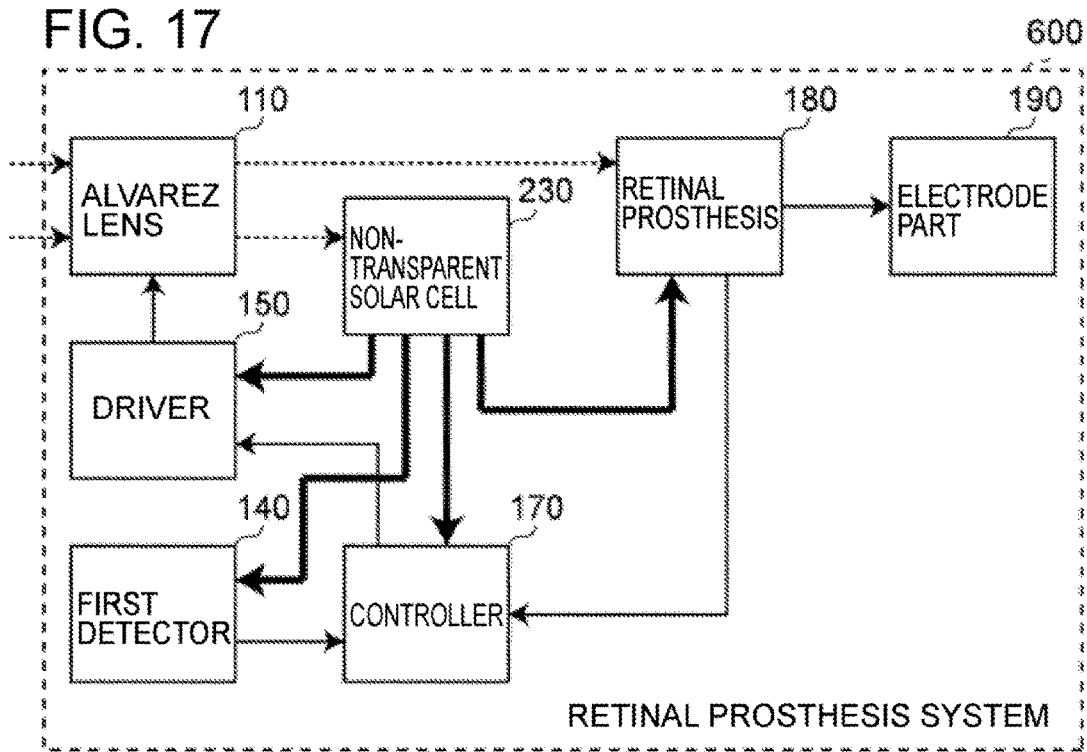
FIG. 17 is a schematic diagram illustrating an example of the configuration of a retinal prosthesis system according to an embodiment.

FIG. 17 is a functional block diagram illustrating an example of the configuration of a retinal prosthesis system according the sixth embodiment. In FIG. 17, like reference numerals designate like parts as in FIG. 4 or 7, and the same description may not be repeated. In FIG. 17, the path of light is indicated by a broken arrow in distinction from the paths of others (e.g., electrical signal, etc.) each indicated by a solid line.

A retinal prosthesis system 600 includes the Alvarez lens 110, the non-transparent solar cell 230, the first detector 140, the driver 150, the controller 170, the retinal prosthesis 180, and the electrode part 190. As with the retinal prosthesis system 300, the retinal prosthesis system 600 is placed in the eye. The retinal prosthesis system 600 is different from the retinal prosthesis system 300 in being provided with the non-transparent solar cell 230 in place of the transparent solar cell 130. As illustrated in FIG. 5 or 6, the non-transparent solar cell 230 is provided with one or more openings 231. The light having transmitted through the Alvarez lens 110 passes through the opening(s) 231 formed in the non-transparent solar cell 230, and reaches the vitreous body 29.

In the retinal prosthesis system 600, a power supply line is provided between the non-transparent solar cell 230 and the first detector 140 to supply electric power generated by the non-transparent solar cell 230. A power supply line is provided between the non-transparent solar cell 230 and the driver 150 to supply electric power generated by the non-transparent solar cell 230. In addition, a power supply line is provided between the non-transparent solar cell 230 and the retinal prosthesis 180 to supply electric power generated by the non-transparent solar cell 230. Further, a power supply line is provided between the non-transparent solar cell 230 and the controller 170 to supply electric power generated by the non-transparent solar cell 230.

In this embodiment, the photoelectric conversion element array of the retinal prosthesis 180 receives the light having passed through the opening(s) 231 formed in the non-transparent solar cell 230, and generates an electrical signal. The opening 231 formed in the non-transparent solar cell 230 may be located in a position opposite to the macula in the retinal prosthesis 180.

In this embodiment, although the non-transparent solar cell 230 is described as being provided with an opening, the non-transparent solar cell 230 may be provided with a cutout. Further, in this embodiment, while the non-transparent solar cell 230 is described as being provided with one or more openings, the transparent solar cell 130 of the third embodiment may be provided with one or more openings or cutouts.

[Effects]

The retinal prosthesis system 600 is an example of the retinal prosthesis system of this embodiment. In addition to the effects of the third embodiment, the retinal prosthesis system of this embodiment has the following advantages.

In the retinal prosthesis system (e.g., the retinal prosthesis system 600), the converter may include a non-transparent solar cell (e.g., the non-transparent solar cell 230) configured to convert the energy of light incident on the eye into electrical energy.

The non-transparent solar cell does not have the function of transmitting light incident on the eye. Light that has not entered the non-transparent solar cell reaches the retinal prosthesis. In the retinal prosthesis system, the driver is placed in the eye and can change the focal length of the lens with the electrical energy received from the converter.

In the retinal prosthesis system, the converter may be provided with an opening (e.g., the opening 231) to let part of light incident on the eye pass therethrough.

In the retinal prosthesis system, the light having passed through the opening can reach the retinal prosthesis. This allows an increase in the size of the light receiving surface of the converter while blocking light traveling to reach the retinal prosthesis as little as possible.

In the retinal prosthesis system, the opening may be formed in a position opposite to the macula in the retinal prosthesis.

With the retinal prosthesis system, it is possible to sufficiently secure the size of the light receiving surface of the converter and the size of the retinal prosthesis.

In the retinal prosthesis system, the photoelectric conversion element array may be configured to receive the light having passed through the opening and generate the electrical signal.

With the retinal prosthesis system, it is possible to secure the size of the light receiving surface of the converter to generate more power. Further, the size of the retinal prosthesis can also be secured. Thus, more information can be transmitted to the visual cortex.

<Seventh Embodiment>

In the sixth embodiment, the opening formed in the non-transparent solar cell 230 may be provided with a lens for adjusting a light flux that reaches the macula. With this, the size of the opening can be adjusted. Therefore, it is possible to secure a large area of the light receiving portion of the non-transparent solar cell 230, for example, resulting in an increase in power to be generated. Besides, if the Alvarez lens 110 is located in front of the non-transparent solar cell 230, it is possible to increase the area of the retinal prosthesis 180 that is placed behind the non-transparent solar cell 230. Accordingly, the size of an image detected by the retinal prosthesis 180 can also be increased. As a result, it is possible to improve the accuracy of control based on the image detected in the retinal prosthesis 180.

Incidentally, the transparent solar cell 130 may also include a lens in the opening for adjusting a light flux that reaches the macular. In this case also, the same effects as above can be achieved.

[Effects]

The retinal prosthesis system described in the seventh embodiment is an example of the retinal prosthesis system of the embodiment. In addition to the effects of the sixth embodiment, the retinal prosthesis system of this embodiment has the following advantages.

In the retinal prosthesis system, the converter (e.g., the transparent solar cell 130 or the non-transparent solar cell 230) may be provided with a lens in the opening for adjusting a light flux that reaches the macula.

With the retinal prosthesis system, it is possible to secure a large area of the light receiving portion of the non-transparent solar cell. Thus, more power can be generated. Further, the size of the retinal prosthesis can be increased. Accordingly, the size of an image detected by the retinal prosthesis can also be increased. As a result, it is possible to improve the accuracy of control based on the image detected in the retinal prosthesis.

(First Modification)

In the above embodiments of the retinal prosthesis system, an example is described in which the spherical diopter power is changed by the Alvarez lens. For another example, the astigmatic power may be changed by the Alvarez lens. For example, in FIG. 8, by relatively moving the optical elements 111 and 112 in the xy plane perpendicular to the axis O in the x direction (horizontal direction), the astigmatic power (refractive power) obtained by optically combining the optical elements 111 and 112 can be continuously changed. In FIG. 8, the optical element 111 is moved to the left (−x direction), while the optical element 112 is moved to the right (+x direction).

Besides, a variable cross cylinder lens may be placed on the incident side of the Alvarez lens 110 to change the astigmatic power. The variable cross cylinder lens is formed of a pair of cylindrical lenses. In this case, by relatively rotating the cylindrical lenses, the astigmatic power obtained by optically combining the cylindrical lenses continuously changes. For example, a known ultrasonic linear motor drives one of the cylindrical lenses to rotate in the normal rotation direction, and drives the other of the cylindrical lenses to rotate in the reverse rotation direction.

Moreover, it is also possible to place a prism, which changes the orientation of a light ray and optical elements capable of changing any of optical properties such as transmission wavelength, transmittance, and magnification, on the incident side or the emission side of the Alvarez lens 110.

(Second Modification)

In the retinal prosthesis system according to the above embodiments or the first modification, an example is described in which an Alvarez lens is used as the variable focus lens, it is not so limited.

Figure 18:
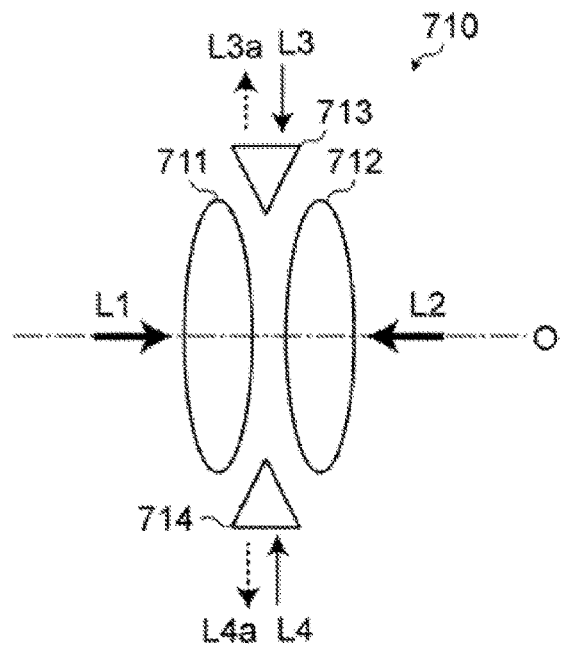
FIG. 18 is a schematic diagram illustrating an example of the configuration of a retinal prosthesis system according to an embodiment.

FIG. 18 is a cross-sectional view illustrating an example of the configuration of a lens according to a second modification. FIG. 18 is a schematic vertical cross-sectional view, passing through the axis O, of the lens of the second modification as viewed from the side.

A lens 710 of the second modification includes a pair of optical elements 711 and 712, and a pair of wedge members (spacers) 713 and 714. The optical elements 711 and 712 are placed such that the predetermined axis O of the lens 710 matches the optical axis. The optical element 711 is biased by a first biasing means (not illustrated) in a first direction L1 along the axis O. The optical element 712 is biased by a second biasing means (not illustrated) in a second direction L2 opposite to the first direction L1 along the axis O. The wedge members 713 and 714 are configured to be movable in a third direction L3 and a fourth direction L4 perpendicular to the first direction L1 and the second direction L2 such that a space between the optical elements 711 and 712 can be changed. Upon increasing the space between the optical elements 711 and 712, the wedge members 713 and 714 are brought close to each other. As a specific example, upon increasing the space between the optical elements 711 and 712, the wedge member 713 is moved in the third direction L3 by the driver 150 based on the drive signal, while the wedge member 714 is moved in the fourth direction L4 by the driver 150 based on the drive signal. Upon reducing the space between the optical elements 711 and 712, the wedge members 713 and 714 are separated from each other. As a specific example, upon reducing the space between the optical elements 711 and 712, the wedge member 713 is moved in a direction L3a opposite to the third direction L3 by the driver 150 based on the drive signal, while the wedge member 714 is moved in a direction L4a opposite to the fourth direction L4 by the driver 150 based on the drive signal. Thereby, in the lens 710 of the second modification, the focal length can be changed by the driver 150. In the above embodiments or the first modification, the lens 710 of the second modification can be used in place of the Alvarez lens 110.

(Third Modification)

In the above embodiments, as a method for changing a program to be executed by the controller, parameters (table information, threshold, etc.), or the like after the placement of the system in the eye, there are an invasive method and a non-invasive (low-invasive) method.

In the invasive method, for example, at least part of the retinal prosthesis system is taken out by surgery, or the retinal prosthesis system is directly manipulated in a predetermined manner by inserting an instrument into the eye to change the parameters, programs, or the like stored therein.

In the non-invasive method, for example, one or more switches, which are controlled in response to light such as laser light (or magnetic force, electromagnetic waves, etc.), are provided in the eye (e.g., on a surface of the controller or the first detector, etc.). The laser light is irradiated from the outside of the eye to thereby change the switching state of the switch(es). A signal is generated according to the switching state of the one or more switches. The first detector and the controller receive the signal, and thus the table information, the threshold, and the programs are changed. The operation content of the switch can be changed by the laser intensity, the irradiation time, the irradiation pattern, or the like. When there are provided a plurality of switches, the operation content may be changed according to the selection of a switch to be operated or the order of switches to be operated.

The configurations described above are mere examples for embodying or carrying out the present invention, and therefore susceptible to several modifications and variations (omission, substitution, addition, etc.), all coming within the scope of the invention.

For example, the configuration of the lens according to the above embodiments or the modifications is not limited to those described in connection with FIG. 8 or 18. Besides, the driver of the above embodiments or the modifications is not limited to those described in connection with FIGS. 9 and 10. For example, the lens may be made of MEMS with the function of an actuator.

The transparent solar cell 130 and the non-transparent solar cell 230 are not limited to those described in the above embodiments or the modifications. For example, a dye-sensitized solar cell may be used as the transparent solar cell 130 and the non-transparent solar cell 230.

A computer program for realizing the above embodiments or the modifications may be stored in an arbitrary recording medium that is readable by a computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like.

The program may be sent/received through a network such as the Internet or LAN.

The invention claimed is:

1. A retinal prosthesis system comprising:
   a converter configured to be placed in an eye, and allow part of light incident on the eye to pass therethrough while converting energy of other part of the light into electrical energy;
   a retinal prosthesis configured to be placed in the eye on a side of the converter opposite from a side of the converter on which light is incident, including a photoelectric conversion element array configured to operate with the electrical energy received from the converter to detect the light having passed through the converter to generate an electrical signal; and
   a transmitter configured to send the electrical signal generated by the retinal prosthesis to visual cortex of brain.

2. The retinal prosthesis system according to claim 1, wherein the converter is provided with an opening to allow the part of the light incident on the eye to pass therethrough.

3. The retinal prosthesis system according to claim 2, wherein the opening is formed in a position opposite to a macula in the retinal prosthesis.

4. The retinal prosthesis system according to claim 2, wherein the converter includes a lens in the opening to adjust a light flux that reaches the macula.

5. The retinal prosthesis system according to claim 1, wherein
   the converter includes a transparent solar cell configured to transmit the part of the light incident on the eye therethrough, and convert the energy of the other part into the electrical energy, and
   at least part of the photoelectric conversion element array is configured to receive the light having transmitted through the transparent solar cell and generate the electrical signal.

6. The retinal prosthesis system according to claim 1, wherein
   the converter includes a non-transparent solar cell configured to allow the part of the light incident on the eye to pass therethrough, and convert the energy of the other part into the electrical energy, and
   at least part of the photoelectric conversion element array is configured to receive the light having passed through the non-transparent solar cell and generate the electrical signal.

* * * * *